United States Patent
Hyde et al.

(10) Patent No.: US 9,730,656 B2
(45) Date of Patent: *Aug. 15, 2017

(54) SYSTEMS, DEVICES, AND METHODS FOR LOWERING DENTAL X-RAY DOSAGE INCLUDING FEEDBACK SENSORS

(71) Applicant: Elwha LLC, Bellevue, WA (US)

(72) Inventors: Roderick A. Hyde, Redmond, WA (US); Edward K. Y. Jung, Bellevue, WA (US); Jordin T. Kare, Seattle, WA (US); Tony S. Pan, Bellevue, WA (US); Charles Whitmer, North Bend, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 221 days.

This patent is subject to a terminal disclaimer.

(21) Appl. No.: 14/201,386

(22) Filed: Mar. 7, 2014

(65) Prior Publication Data
US 2015/0250433 A1    Sep. 10, 2015

(51) Int. Cl.
*A61B 6/14* (2006.01)
*H01L 27/146* (2006.01)
(Continued)

(52) U.S. Cl.
CPC ............ *A61B 6/145* (2013.01); *A61B 5/0088* (2013.01); *A61B 5/682* (2013.01); *A61B 6/14* (2013.01);
(Continued)

(58) Field of Classification Search
CPC .. H01J 37/3045; H01J 37/304; H01J 37/3023; H01J 37/302; H01J 37/244; H01J 37/09; H01J 37/023; H01J 37/02; H01J 35/00; H01J 35/02; H01J 35/16; H01J 37/00; H01J 37/147; H01J 37/16; H01J 37/20; H01J 37/22; H01J 37/222;
(Continued)

(56) References Cited

U.S. PATENT DOCUMENTS 4,223,228 A    9/1980 Kaplan
4,223,229 A    9/1980 Persico et al.
(Continued)

OTHER PUBLICATIONS

Basavaraju et al.; Red persistent luminescence in $MgGa_2O_4:Cr^{3+}$; a new phosphor for in vivo imaging; J. Phys. D: Appl. Phys.; bearing a date of Aug. 30, 2013; pp. 1-5; vol. 46; IOP Publishing Ltd.
(Continued)

*Primary Examiner* — Anastasia Midkiff
(74) *Attorney, Agent, or Firm* — Daniel J. Honz; Advent, LLP

(57) ABSTRACT

Systems, devices, and methods are described for providing, among other things, an intra-oral x-ray imaging system configured to reduce patient exposure to x-rays, reduce amount of scatter, transmission, or re-radiation during imaging, or improve x-ray image quality. In an embodiment, an intra-oral x-ray imaging system includes an intra-oral x-ray sensor configured to communicate intra-oral x-ray sensor position information or intra-oral x-ray sensor orientation information to a remote x-ray source.

38 Claims, 10 Drawing Sheets

(51) Int. Cl.
| | |
|---|---|
| *H01L 27/148* | (2006.01) |
| *G21F 1/08* | (2006.01) |
| *G03B 42/04* | (2006.01) |
| *G01T 1/24* | (2006.01) |
| *H01J 37/244* | (2006.01) |
| *H01J 37/304* | (2006.01) |
| *A61B 5/00* | (2006.01) |
| *A61B 6/06* | (2006.01) |
| *A61B 6/00* | (2006.01) |
| *A61B 6/10* | (2006.01) |
| *A61B 90/00* | (2016.01) |
| *G21F 1/02* | (2006.01) |

(52) U.S. Cl.
CPC .............. *A61B 6/547* (2013.01); *A61B 6/587* (2013.01); *G01T 1/244* (2013.01); *G03B 42/047* (2013.01); *G21F 1/085* (2013.01); *H01J 37/244* (2013.01); *H01J 37/3045* (2013.01); *H01L 27/14601* (2013.01); *H01L 27/14623* (2013.01); *H01L 27/14806* (2013.01); *H01L 27/14818* (2013.01); *A61B 6/06* (2013.01); *A61B 6/107* (2013.01); *A61B 6/4035* (2013.01); *A61B 6/4208* (2013.01); *A61B 6/467* (2013.01); *A61B 6/487* (2013.01); *A61B 6/542* (2013.01); *A61B 2090/0436* (2016.02); *A61B 2090/0481* (2016.02); *A61B 2562/164* (2013.01); *G01T 1/24* (2013.01); *G03B 42/042* (2013.01); *G21F 1/026* (2013.01); *G21F 1/08* (2013.01); *H01L 27/14618* (2013.01); *H01L 27/14658* (2013.01)

(58) Field of Classification Search
CPC ......... H01J 2237/045; H01J 2237/0451; H01J 2237/0453; H01J 2237/0455; H01J 2237/083; H01J 2237/0835; H01J 2237/24; A61B 6/06; A61B 6/08; A61B 6/14; A61B 6/145; A61B 6/4035; A61B 6/4042; A61B 6/50; A61B 6/501; A61B 6/54; A61B 6/542; A61B 6/545; A61B 6/547; A61B 6/04; A61B 6/0492; A61B 6/42; A61B 6/4208; A61B 6/425; A61B 6/44; A61B 6/4494; A61B 6/587; G21K 1/00; G21K 1/02; G21K 1/04; G21K 1/043; G21K 1/046; G21K 5/00; G21K 5/04; G03B 42/04; G03B 42/042; G03B 42/047; G03B 42/00; G03B 42/02; G03B 42/025; G03B 2207/00; A61N 5/1048; A61N 5/1049; A61N 5/1064; A61N 2005/105; A61N 2005/1051; A61N 2005/1059; A61N 2005/1095; H05G 1/00; H05G 1/02; H05G 1/04; G02B 5/00; G02B 5/005; G02B 27/00; G02B 27/0081; G02B 27/09; G02B 27/0938; G02B 27/0988; G02B 27/30; G02B 27/40; G02B 27/64; G02B 2207/125; G01T 1/00; G01T 1/16; H01L 27/144; H01L 27/146; H01L 27/14601; H01L 27/14625; H01L 27/14629; H01L 27/14658; H01L 27/14676; H01L 27/148; H01L 27/14806; H01L 27/305; H01L 27/307; H01L 27/308; H01L 31/00; H01L 31/02; H01L 31/12; H01L 31/14; H01L 31/16; H01L 31/20; H01L 31/22
USPC ..... 379/19, 38–40, 91, 98.2, 98.3, 145, 147, 379/150–153, 156–158, 160, 189–191, 379/204–206, 210; 250/491.1
See application file for complete search history.

(56) References Cited

U.S. PATENT DOCUMENTS

| | | | |
|---|---|---|---|
| 4,475,224 A | 10/1984 | Grassme | |
| 4,501,010 A | 2/1985 | Grassme | |
| 4,813,060 A | 3/1989 | Heubeck et al. | |
| 5,463,669 A | 10/1995 | Kaplan | |
| 5,828,722 A * | 10/1998 | Ploetz | A61B 6/08 378/170 |
| 6,042,267 A * | 3/2000 | Muraki | G01T 1/2018 348/E5.086 |
| 6,097,423 A * | 8/2000 | Mattsson-Boze | A61B 1/00045 348/65 |
| 6,122,538 A * | 9/2000 | Sliwa, Jr. | A61B 8/00 324/207.14 |
| 6,266,142 B1 * | 7/2001 | Junkins | G01S 5/163 250/559.14 |
| 6,625,896 B1 * | 9/2003 | Olson | G01C 9/06 33/366.11 |
| 7,092,483 B2 | 8/2006 | Nyholm | |
| 7,503,692 B2 | 3/2009 | De Godzinsky | |
| 7,580,502 B2 | 8/2009 | Dalpiaz et al. | |
| 7,715,525 B2 | 5/2010 | Spartiotis et al. | |
| 7,715,526 B2 | 5/2010 | Spartiotis et al. | |
| 7,775,713 B2 * | 8/2010 | Klemola | A61B 6/145 378/168 |
| 7,780,350 B2 * | 8/2010 | Tranchant | G05B 19/401 378/205 |
| 7,945,016 B2 | 5/2011 | Bothorel et al. | |
| 7,997,796 B2 | 8/2011 | De Godzinsky | |
| 2003/0026387 A1 * | 2/2003 | Makila | A61B 6/488 378/168 |
| 2003/0030721 A1 | 2/2003 | Nyholm | |
| 2003/0138078 A1 * | 7/2003 | Eberhard | G21K 1/04 378/145 |
| 2004/0213382 A1 | 10/2004 | Andell et al. | |
| 2005/0031086 A1 | 2/2005 | Dalpiaz et al. | |
| 2005/0128465 A1 | 6/2005 | Skultety-Betz et al. | |
| 2005/0135558 A1 * | 6/2005 | Claus | A61B 6/02 378/42 |
| 2005/0276380 A1 * | 12/2005 | Varjonen | A61B 6/145 378/98.9 |
| 2006/0251210 A1 * | 11/2006 | Chao | A61B 6/585 378/19 |
| 2007/0080308 A1 | 4/2007 | Mousavi Yeganeh | |
| 2007/0223649 A1 | 9/2007 | De Godzinsky | |
| 2007/0286527 A1 * | 12/2007 | Jabri | A61B 6/06 382/286 |
| 2008/0002808 A1 | 1/2008 | De Godzinsky | |
| 2008/0013106 A1 * | 1/2008 | Sidor | G01D 3/036 356/622 |
| 2009/0232274 A1 | 9/2009 | Spartiotis et al. | |
| 2009/0232275 A1 | 9/2009 | Spartiotis et al. | |
| 2010/0034340 A1 | 2/2010 | Spartiotis et al. | |
| 2010/0074402 A1 | 3/2010 | Bothorel et al. | |
| 2010/0074403 A1 | 3/2010 | Inglese et al. | |
| 2010/0278299 A1 | 11/2010 | Loustauneau et al. | |
| 2011/0150185 A1 | 6/2011 | Uzbelger Feldman | |
| 2012/0243762 A1 * | 9/2012 | Kanerva | A61B 6/03 382/131 |
| 2013/0163718 A1 * | 6/2013 | Lindenberg | G01B 11/25 378/39 |
| 2014/0010349 A1 * | 1/2014 | De Godzinsky | A61B 6/06 378/62 |
| 2014/0010350 A1 * | 1/2014 | De Godzinsky | A61B 6/06 378/62 |

OTHER PUBLICATIONS

Zhao et al.; X-ray imaging performance of structured cesium iodide scintillators; Medical Physics; bearing a date of Aug. 26, 2004 and Sep. 2004; pp. 2594-2605; vol. 31, No. 9; Am. Assoc. Phys. Med.

\* cited by examiner

FIG. 4B  400

430
- 444 varying a separation between a collimator aperture and an x-ray beam emitter within x-ray source
- 446 varying an orientation between a collimator aperture and an x-ray source
- 448 actuating one or more selective-actuatable absorber blades forming part of a focal plane shutter
- 450 actuating an x-ray beam limiter assembly configured to adjust an x-ray beam field size
- 452 generating one or more parameters associated with an x-ray beam field size adjustment responsive to automatically determining the intra-oral x-ray sensor border position and the intra-oral x-ray sensor orientation
- 454 generating one or more x-ray beam limiter assembly setting parameters responsive to automatically determining the intra-oral x-ray sensor border position and the intra-oral x-ray sensor orientation
- 456 actuating at least one liquid absorber 460
- acquiring intra-oral x-ray image information associated with a patient
- 462 acquiring one or more intra-oral radiographic images
- 464 acquiring intra-oral radiographic view information
- 466 acquiring a periapical view image of at least one anterior or posterior tooth
- 468 acquiring a bitewing view image of at least one tooth crown
- 470 acquiring an occlusal view image of a palate
- 472 acquiring a posterior periapical image
- 474 acquiring an anterior periapical image 478 generating at least one parameter associated with an x-ray imaging mode responsive to automatically determining the intra-oral x-ray sensor border position and the intra-oral x-ray sensor orientation

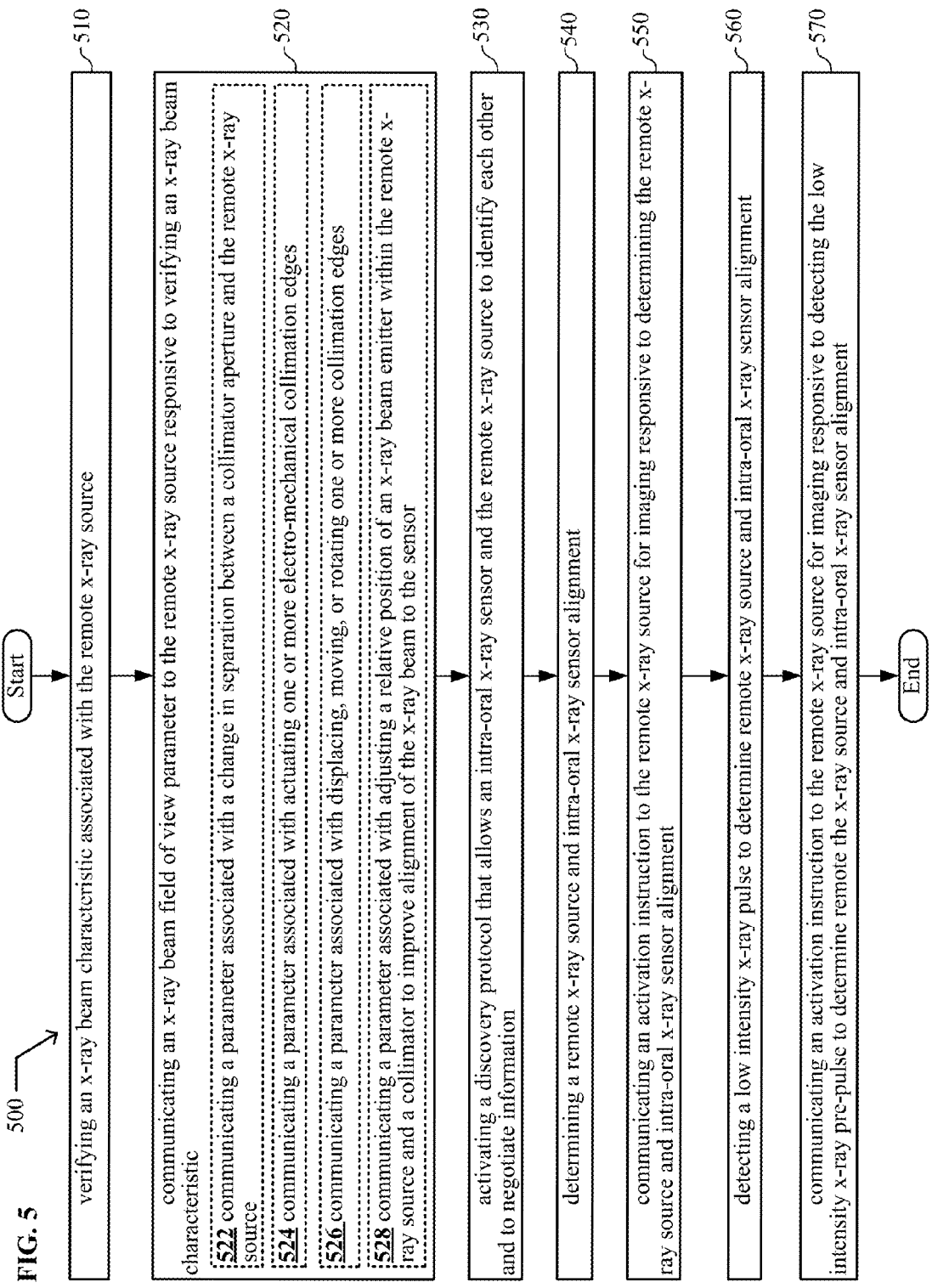

SYSTEMS, DEVICES, AND METHODS FOR LOWERING DENTAL X-RAY DOSAGE INCLUDING FEEDBACK SENSORS

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In an aspect, the present disclosure is directed to, among other things, an intra-oral x-ray imaging system. In an embodiment, the intra-oral x-ray imaging system includes an intra-oral x-ray sensor configured to acquire intra-oral x-ray image information associated with a patient. In an embodiment, the intra-oral x-ray imaging system includes an x-ray beam limiter assembly including a controllable x-ray collimator module. In an embodiment, the controllable x-ray collimator module includes an x-ray beam collimation adjustment mechanism that is responsive to one or more inputs including information associated with a border position of the intra-oral sensor. In an embodiment, the intra-oral x-ray imaging system includes an x-ray beam limiter assembly configured to adjust an x-ray beam field of view. In an embodiment, the intra-oral x-ray imaging system includes an x-ray collimator module operably coupled to the intra-oral x-ray sensor and the x-ray beam limiter assembly. In an embodiment, the x-ray collimator module is configured to adjust an x-ray beam field of view responsive to one or more inputs including information associated with a border position of the intra-oral sensor. In an embodiment, the intra-oral x-ray imaging system includes an x-ray beam limiter assembly having one or more shutters (e.g., spring-loaded shutters, solenoid activated shutters, relay device activated shutters, electro-mechanical shutters, etc.). In an embodiment, during operation, the x-ray collimator module is configured to vary a shutter aperture associated with at least one of the one or more shutters responsive to the one or more inputs. In an embodiment, the intra-oral x-ray imaging system includes an x-ray beam limiter assembly having one or more aperture diaphragms. In an embodiment, during operation, the x-ray collimator module is configured to vary a diaphragm aperture of the one or more aperture diaphragms responsive to one or more inputs including information associated with a border position of the intra-oral sensor.

In an aspect, the present disclosure is directed to, among other things, an intra-oral x-ray imaging device. In an embodiment, the intra-oral x-ray imaging device includes circuitry configured to determine a position (e.g., location, spatial placement, locality, spatial location, physical location, physical position, etc.) or an orientation (e.g., angular position, physical orientation, attitude, etc.) of an intra-oral x-ray sensor. In an embodiment, the intra-oral x-ray imaging device includes circuitry configured to adjust an x-ray beam field of view responsive to one or more inputs from the circuitry configured to determine the position or orientation of the intra-oral x-ray sensor. In an embodiment, the intra-oral x-ray imaging device includes circuitry configured to acquire intra-oral x-ray image information associated with a patient. In an embodiment, the intra-oral x-ray imaging device includes circuitry configured to generate one or more parameters associated with a field of view setting.

In an aspect, the present disclosure is directed to, among other things, an intra-oral x-ray imaging method. In an embodiment, the intra-oral x-ray imaging method includes automatically determining an intra-oral x-ray sensor border position and an intra-oral x-ray sensor orientation. In an embodiment, the intra-oral x-ray imaging method includes varying an x-ray beam field of view parameter (e.g., a field of view size, a diameter dimension, a field of view position parameter, an x-ray field collimation parameter, etc.) responsive to one or more inputs including information associated with the intra-oral x-ray sensor border position and the intra-oral x-ray sensor orientation. In an embodiment, the intra-oral x-ray imaging method includes acquiring intra-oral x-ray image information associated with a patient. In an embodiment, the intra-oral x-ray imaging method includes generating at least one parameter associated with an x-ray imaging mode (e.g., adult panoramic mode, child panoramic mode, high-dose-rate mode, low-dose-rate mode, moderate-dose-rate mode, mandible mode, occlusion mode, maxillary mode, panoramic mode, pulsed fluoroscopy mode, temporomandibular joint mode, etc.) responsive to automatically determining the intra-oral x-ray sensor border position and the intra-oral x-ray sensor orientation. In an embodiment, the intra-oral x-ray imaging method includes varying an x-ray beam aim parameter responsive to automatically determining the intra-oral x-ray sensor border position and the intra-oral x-ray sensor orientation.

In an aspect, the present disclosure is directed to, among other things, an intra-oral x-ray sensor. In an embodiment, the intra-oral x-ray sensor includes an x-ray image component configured to acquire intra-oral x-ray image information associated with a patient. In an embodiment, the intra-oral x-ray sensor includes an intra-oral radiation shield structure configured to reduce at least one of x-ray scattering, transmission, or re-radiation by at least 50%. For example, in an embodiment, oral x-ray sensor includes an intra-oral radiation shield structure having one or more high-atomic number (high-Z) materials in an amount sufficient to reduce at least one of x-ray scattering, transmission, or re-radiation by at least 50%.

In an aspect, the present disclosure is directed to, among other things, an intra-oral x-ray sensor. In an embodiment, the intra-oral x-ray sensor includes circuitry configured to communicate intra-oral x-ray sensor position information to a remote x-ray source. In an embodiment, the circuitry configured to communicate intra-oral x-ray sensor position information to the remote x-ray source includes one or more wired or wireless connections to the remote x-ray source. In an embodiment, the intra-oral x-ray sensor includes circuitry configured to communicate intra-oral x-ray sensor orientation information to the remote x-ray source. In an embodiment, the intra-oral x-ray sensor includes circuitry configured to verify an x-ray beam characteristic associated with the remote x-ray source. In an embodiment, the intra-oral x-ray sensor includes circuitry configured to communicate an x-ray beam field of view parameter to the remote x-ray source responsive to verifying an x-ray beam characteristic. In an embodiment, the intra-oral x-ray sensor includes circuitry configured to determine remote x-ray source and intra-oral x-ray sensor alignment before communicating an activation instruction to the remote x-ray source for imaging. In an embodiment, the intra-oral x-ray sensor includes circuitry configured to acquire a low intensity x-ray pulse to determine remote x-ray source and intra-oral x-ray sensor alignment before communicating an activation instruction to the remote x-ray source for imaging.

In an aspect, the present disclosure is directed to, among other things, an intra-oral x-ray sensor operation method. In an embodiment, the intra-oral x-ray sensor operation method includes communicating intra-oral x-ray sensor position information to a remote x-ray source. In an embodiment, the intra-oral x-ray sensor operation method includes communicating intra-oral x-ray sensor orientation information to a remote x-ray source. In an embodiment, the intra-oral x-ray sensor operation method includes verifying an x-ray beam characteristic associated with the remote x-ray source. In an embodiment, the intra-oral x-ray sensor operation method includes communicating an x-ray beam field of view parameter to the remote x-ray source responsive to verifying an x-ray beam characteristic.

BRIEF DESCRIPTION OF THE FIGURES

FIGS. 4A-4C show a flow diagram of an intra-oral x-ray imaging method according to one embodiment.

FIG. 5 shows a flow diagram of an intra-oral x-ray sensor operation method according to one embodiment.

DETAILED DESCRIPTION

Figure 1A:
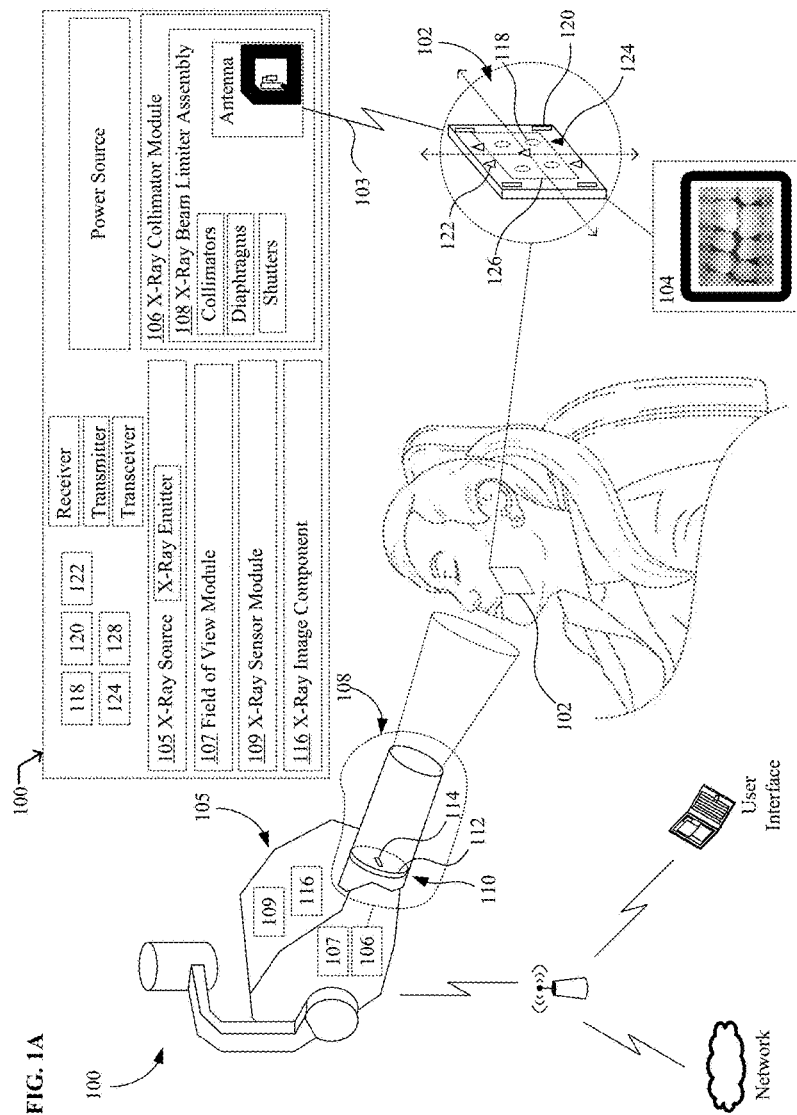
FIG. 1A is a perspective view of an intra-oral x-ray imaging system according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Radiographs (e.g., intra-oral radiographs, panoramic radiographs, cephalo radiographs, etc.) are essential and valuable diagnostic tools in dentistry. An objective of dental radiography is to obtain the highest quality images possible, while keeping patients' exposure risk to a minimum. Exposure to radiation may cause cancer, birth defects in the children of exposed parents, and cataracts. A major concern is the delayed health effects arising from chronic cumulative exposure to radiation. One way to reduce a patient's radiation burden is to employ low-dose practices.

Figure 1B:
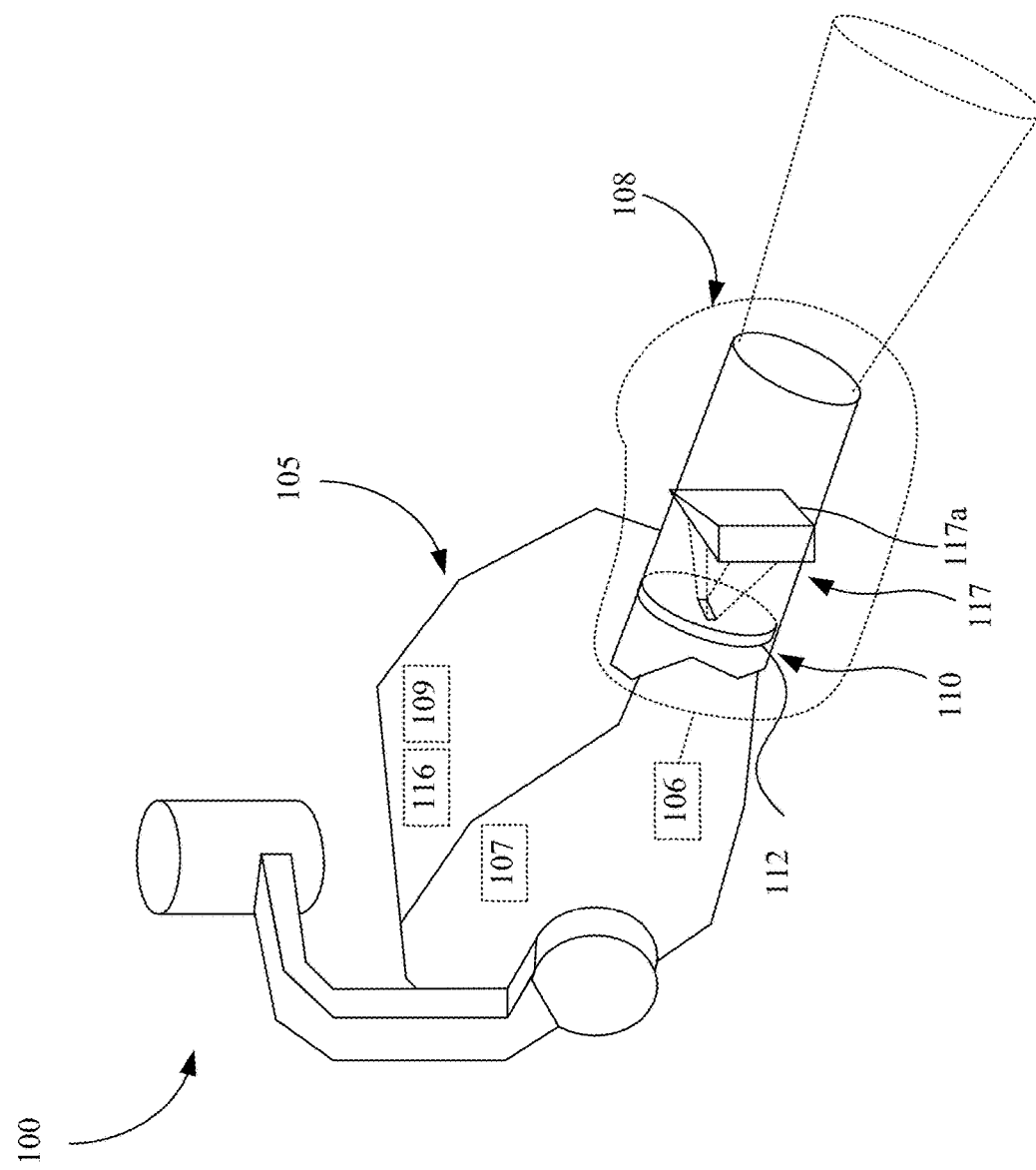
FIG. 1B is a perspective view of an intra-oral x-ray imaging system according to one embodiment.

FIGS. 1A and 1B show an intra-oral x-ray imaging system 100 in which one or more methodologies or technologies can be implemented such as, for example, reducing patient exposure to x-rays, reducing amount of scatter, transmission, or re-radiation during imaging, or improving x-ray image quality. In an embodiment, the intra-oral x-ray imaging system 100 includes one or more intra-oral x-ray sensors 102. In an embodiment, at least one of the one or more intra-oral x-ray sensors 102 is configured to acquire intra-oral x-ray image information 104 associated with a patient. In an embodiment, the intra-oral x-ray imaging system 100 includes an x-ray source 105 operably coupled to one or more intra-oral x-ray sensors 102. In an embodiment, the intra-oral x-ray imaging system 100 includes one or more power sources. In an embodiment, during operation, x rays from the x-ray source 105 pass through the body of the patient striking hard and soft tissue. In an embodiment, a portion of the x-ray beam is deflected, a portion of the x-ray beam is scattered, a portion of the x-ray beam is absorbed, a portion triggers release of characteristic radiation, etc. Intra-oral x-ray image information (e.g., diagnostic dental x rays) is acquired by positioning a part of the body to be examined between a focused x-ray beam and the intra-oral x-ray sensors 102.

In an embodiment, the intra-oral x-ray imaging system 100 includes one or more modules. For example, in an embodiment, the intra-oral x-ray imaging system 100 includes x-ray collimator module 106. In an embodiment, the collimator module 106 is operably coupled to an intra-oral x-ray sensor 102 and an x-ray beam limiter assembly 108. For example, in an embodiment, the collimator module 106 is operably coupled to an intra-oral x-ray sensor 102 via a wired or wireless connection 103. In an embodiment, the x-ray beam limiter assembly 108 includes a controllable x-ray collimator module 106. In an embodiment, the controllable x-ray collimator module 106 includes an x-ray beam collimation adjustment mechanism that is responsive to one or more inputs including information associated with a border position of the intra-oral sensor 102. For example, in an embodiment, the x-ray collimator module 106 is configured to vary a shutter aperture 114 associated with at least one of the one or more shutters responsive one or more inputs including information associated with a position of the intra-oral sensor 102, a border position of the intra-oral sensor 102, a position of an intra-oral x-ray sensor centroid, or the like.

In an embodiment, a module includes, among other things, one or more computing devices such as a processor (e.g., a microprocessor), a central processing unit (CPU), a digital signal processor (DSP), an application-specific integrated circuit (ASIC), a field programmable gate array (FPGA), or the like, or any combinations thereof, and can include discrete digital or analog circuit elements or electronics, or combinations thereof. In an embodiment, a module includes one or more ASICs having a plurality of predefined logic components. In an embodiment, a module includes one or more FPGAs, each having a plurality of programmable logic components.

In an embodiment, the x-ray collimator module 106 includes a module having one or more components operably coupled (e.g., communicatively, electromagnetically, magnetically, ultrasonically, optically, inductively, electrically, capacitively coupled, or the like) to each other. In an embodiment, a module includes one or more remotely located components. In an embodiment, remotely located components are operably coupled, for example, via wireless communication. In an embodiment, remotely located components are operably coupled, for example, via one or more receivers, transmitters, transceivers, antennas, or the like. In an embodiment, the x-ray collimator module 106 includes a module having one or more routines, components, data structures, interfaces, and the like.

In an embodiment, a module includes memory that, for example, stores instructions or information. For example, in an embodiment, the x-ray collimator module 106 includes memory that stores, for example, one or more of intra-oral x-ray sensor border position information, intra-oral x-ray sensor centroid information, intra-oral x-ray sensor dimension information, intra-oral x-ray sensor orientation information, intra-oral x-ray sensor position information, intra-oral x-ray sensor specific collimation information, or the like. For example, in an embodiment, the x-ray collimator module 106 includes memory that, for example, stores reference collimation information (e.g., reference collimation shape information, reference collimation size information, reference collimation separation information, etc.), intra-oral x-ray sensor position or orientation information, x-ray image information associated with a patient, or the like.

Non-limiting examples of memory include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of memory include Erasable Programmable Read-Only Memory (EPROM), flash memory, or the like. In an embodiment, the memory is coupled to, for example, one or more computing devices by one or more instructions, information, or power buses. For example, in an embodiment, the x-ray collimator module 106 includes memory that, for example, stores reference collimation information (e.g., reference collimation shape information, reference collimation size information, reference collimation separation information, etc.), intra-oral x-ray sensor position or orientation information, x-ray image information associated with a patient, or the like.

In an embodiment, a module includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In an embodiment, a module includes one or more user input/output components, user interfaces, or the like, that are operably coupled to at least one computing device configured to control (electrical, electromechanical, software-implemented, firmware-implemented, or other control, or combinations thereof) at least one parameter associated with, for example, controlling activating, operating, or the like, an x-ray beam limiter assembly 108.

In an embodiment, a module includes a computer-readable media drive or memory slot that is configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, or the like, as well as transmission type medium such as a digital or an analog communication medium (e.g., a fiber optic cable, a waveguide, a wired communications link, a wireless communication link (e.g., receiver, transmitter, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

In an embodiment, the x-ray collimator module 106 is configured to adjust an x-ray beam field of view responsive to one or more inputs including information associated with a border position of the intra-oral sensor 102. For example, in an embodiment, the intra-oral x-ray imaging system 100 includes an x-ray beam limiter assembly 108 having at least one collimator 110. In an embodiment, the collimator 110 includes a barrier 112 with a variable aperture 114 configured to vary the size and shape of an x-ray beam so as to substantially match the size of an intra-oral x-ray sensor detection region 126a (shown in FIG. 2B). In an embodiment, the collimator 110 implements filtration and collimation techniques and methodologies that reduce a patient's radiation burden. For example, in an embodiment, during operation, activation of the collimator 110 results in a reduction of the size and shape of the x-ray beam, resulting in a reduction of the volume of irradiated tissue in the patient. In an embodiment, activation of the collimator 110 also results in the elimination of one or more divergent portion of an x-ray beam.

In an embodiment, the x-ray collimator module 106 is operably coupled to the intra-oral x-ray sensor 102 and the x-ray beam limiter assembly 108, and is configured to adjust an x-ray beam field of view responsive to one or more inputs from the intra-oral x-ray sensor 102 indicative of a border position of the intra-oral sensor 102. The variation of the x-ray beam field of view can comprise a change in the beam size, the beam shape, the beam orientation, or the like. In an embodiment, the x-ray beam expands as it propagates from the x-ray beam limiter assembly 108 towards the patient and the intra-oral x-ray sensor 102. For example, the x-ray propagation can be calculated by assuming straight line x-ray trajectories, allowing the propagation and expansion of the beam to be calculated by knowledge of the relative positions of the x-ray source 105 (e.g., internal components such as an x-ray beam emitter and elements of the x-ray beam limiter assembly 108) and the intra-oral x-ray sensor 102. In an embodiment, the x-ray collimator module 106 is configured to adjust the x-ray beam field of view such that a border position of the expanding x-ray substantially corresponds (e.g., matches, minimizes overfilling, minimizes underfilling, substantially fills the sensor area, etc.) to a border position of the intra-oral x-ray sensor 102 as the propagating beam arrives at it.

In an embodiment, the intra-oral x-ray imaging system 100 includes an x-ray beam limiter assembly 108 having an automatic aperture control mechanism including one or more mechanical diaphragms, (e.g., spring-loaded diaphragm, solenoid activated diaphragm, relay device activated diaphragm, electro-mechanical diaphragm, electromagnetic diaphragm, etc.) The mechanical diaphragm can include a plurality of aperture blades that interact with each other to create the aperture through which the x-rays are projected. In an embodiment, the x-ray collimator module 106 is configured to vary an aperture 114 associated with at least one of the one or more aperture blades included in a mechanical diaphragm responsive one or more inputs indicative of a position of the intra-oral sensor 102, a border position of the intra-oral sensor 102, a position of an intra-oral x-ray sensor centroid, or the like. In an embodiment, the x-ray collimator module 106 is configured to vary an aperture 114 associated with at least one of the one or more mechanical aperture diaphragms responsive one or more inputs indicative of an orientation of the intra-oral sensor 102. In an embodiment, the intra-oral x-ray imaging system 100 includes an x-ray beam limiter assembly 108 having one or more aperture diaphragms. In an embodiment, the x-ray collimator module 106 is configured to vary a diaphragm aperture of the one or more aperture diaphragms responsive to one or more inputs indicative of an orientation or a border position of the intra-oral sensor 102. The diaphragm adjusts the aperture blades to provide the appropriately sized and shaped aperture.

In an embodiment, the intra-oral x-ray imaging system 100 includes an x-ray beam limiter assembly 108 having a collimator 110 including a collimator aperture. In an embodiment, the collimator aperture shape can be a geometrical shape including and regular geometric shapes, such as circular, rectangular, triangular, or the like, as well as irregular geometric shapes. In an embodiment, the intra-oral x-ray imaging system 100 includes an x-ray beam limiter assembly 108 including one or more blades, radiation source shutters, wedges, and the like. In an embodiment, the x-ray collimator module 106 is configured to adjust the x-ray beam field size by actuating a change in a separation distance between a collimator aperture and an x-ray source 105 responsive to one or more inputs including information associated with an orientation or a border position of the intra-oral sensor 102. For example, in an embodiment, the x-ray collimator module 106 is operably coupled to a separation distance adjustment mechanism responsive to one or more inputs including information associated with an orientation or a border position of the intra-oral sensor 102. In an embodiment, the x-ray collimator module 106 is operably coupled to a collimator-and-x-ray source assembly configured to adjust the x-ray beam field size by actuating a change in a separation distance between a collimator aperture and an x-ray source 105 responsive to one or more inputs including information associated with an orientation or a border position of the intra-oral sensor 102.

In an embodiment, the x-ray beam limiter assembly 108 includes a primary collimator and a secondary collimator. In an embodiment, the x-ray beam limiter assembly 108 includes a variable aperture collimator.

In an embodiment, the intra-oral x-ray imaging system 100 includes an x-ray beam limiter assembly 108 having a plurality of selectively actuatable absorber blades configured to form a focal plane shutter. In an embodiment, the focal plane shutter is positioned immediately or right in front of the intra-oral sensor 102. In an embodiment, the focal plane shutter is positioned immediately or right in front of a film-based analog x-ray sensor, a dental digital x-ray sensor, a charge-coupled device (CCD) sensor, complementary metal-oxide-semiconductor (CMOS) sensor, and the like.

In an embodiment, the x-ray collimator module 106 is configured to adjust the x-ray beam field size by actuating one or more of the plurality of selectively actuatable absorber blades responsive one or more inputs including information associated with an orientation or a border position of the intra-oral sensor 102. In an embodiment, the intra-oral x-ray imaging system 100 includes an x-ray beam limiter assembly 108 configured to adjust an x-ray beam field size. In an embodiment, the intra-oral x-ray imaging system 100 includes an x-ray beam limiter assembly 108 configured to reduce the size of the x-ray beam at the point of contact with the intra-oral sensor to the size of the intra-oral sensor 102 detection area so as to reduce a patient exposure to x-rays.

In an embodiment, the x-ray beam limiter assembly 108 includes one or more aperture diaphragms. In an embodiment, the x-ray beam limiter assembly 108 includes one or more circular aperture diaphragms having mechanical extensions (e.g., aperture blades, radiation source shutters, wedges, etc.) configured to form part of a focal plane shutter. In an embodiment, the x-ray beam limiter assembly 108 includes a shutter assembly having one or more opposing pair shutters. In an embodiment, the x-ray beam limiter assembly 108 includes at least a first-stage shutter and a second-stage shutter.

In an embodiment, the intra-oral sensor 102 is configured to work together with the x-ray source 105 to reduce unnecessary patient exposure to x-rays. For example, in an embodiment, the x-ray beam limiter assembly 108 includes an aperture shaped and sized to direct an x-ray beam that provides a beam area that coincides with the detector area of the intra-oral sensor 102. During operation, the x-ray emitter and the intra-oral sensor 102 placed in the patient's mouth may not align exactly, resulting in an x-ray beam projection that is too big, too small, misoriented, etc. In an embodiment, this is fixed by translating or rotating an aperture or by translating or rotating the x-ray emitter. In an embodiment, the x-ray beam limiter assembly 108 includes at least one x-ray beam-limiting aperture configured to translate (laterally and/or longitudinally) relative to an x-ray emitter. In an embodiment, the x-ray beam limiter assembly 108 includes at least one x-ray beam-limiting aperture configured to rotate relative to an x-ray emitter. In an embodiment, the x-ray beam limiter assembly 108 includes at least one x-ray emitter configured to translate (laterally and/or longitudinally) relative to an x-ray beam-limiting aperture.

In an embodiment, the x-ray beam limiter assembly 108 includes one or more diaphragms formed from high atomic number (high-Z) materials. For example, in an embodiment, the x-ray beam limiter assembly 108 includes one or more shutters formed from materials including elements have an atomic number greater than or equal to 37 (Rubidium or higher). In an embodiment, the x-ray beam limiter assembly 108 includes one or more shutters formed from materials including elements have an atomic number greater than or equal to 72 (Hathium or higher).

In an embodiment, the x-ray beam limiter assembly 108 includes one or more x-ray filters. For example, in an embodiment, the intra-oral x-ray imaging system 100 includes an x-ray beam limiter assembly 108 including one or more x-ray compensating filters 117 such as a wedge 117*a* formed from aluminum, ceramic, high-density plastic, etc., that is placed over an oral cavity region during radiography to compensate for differences in radiopacity. In an embodiment, the x-ray compensating filter is configured to limit the x-rays passing through based upon the varying thickness of the filter.

In an embodiment, the intra-oral x-ray imaging system 100 includes an x-ray beam limiter assembly 108 including one or more positive beam limitation devices configured to automatically collimate the x-ray beam to the size of the intra-oral x-ray sensor detection region at the point of contact with the intra-oral x-ray sensor 102. In an embodiment, the intra-oral x-ray imaging system 100 includes an x-ray beam limiter assembly 108 including one or more positive beam limitation devices configured to automatically collimate the x-ray beam so as to substantially match the size of an intra-oral x-ray sensor detection region 126*a* (shown in FIG. 2B).

In an embodiment, the x-ray beam limiter assembly 108 includes an extension cone or an extension cylinder.

In an embodiment, the x-ray collimator module 106 is configured to interface with one or more components via one or more wired or wireless connections. For example, in an embodiment, the x-ray collimator module 106 is in wireless communication with the x-ray beam limiter assembly 108. In an embodiment, the x-ray collimator module 106 is operably coupled to the x-ray beam limiter assembly 108 via one or more wired connections. In an embodiment, the x-ray collimator module 106 is in wireless communication with the intra-oral x-ray sensor 102. In an embodiment, the x-ray collimator module 106 is in wireless communication with an x-ray source 105. In an embodiment, the intra-oral x-ray sensor 102 is in wireless communication with an x-ray source 105.

In an embodiment, the x-ray collimator module 106 is configured to adjust the x-ray beam field size responsive to the one or more inputs, such as one or more inputs including information associated with a location of a corner position of the intra-oral x-ray sensor 102. In an embodiment, the x-ray collimator module 106 is configured to adjust the x-ray beam field size responsive to the one or more inputs including information associated with a location of an edge position of the intra-oral x-ray sensor 102. In an embodiment, the x-ray collimator module 106 is configured to adjust the x-ray beam field size responsive to the one or more inputs including information associated with a location of a reference position on the intra-oral x-ray sensor 102 having a specified offset from a corner of the intra-oral x-ray sensor 102. In an embodiment, the x-ray collimator module 106 is configured to adjust the x-ray beam field size responsive to the one or more inputs including information associated with a location of a reference position on the intra-oral x-ray sensor having a specified offset from an edge of the intra-oral x-ray sensor 102. In an embodiment, the x-ray collimator module 106 is configured to adjust the x-ray beam field size responsive to the one or more inputs including information associated with an edge orientation of the intra-oral x-ray sensor 102.

In an embodiment, the x-ray collimator module 106 is configured to adjust the x-ray beam field size responsive to one or more inputs from the x-ray collimator module 106 indicative of an intra-oral x-ray sensor position or orientation. In an embodiment, the position and/or orientation of the intra-oral x-ray sensor is determined relative to the position and/or orientation of at least one of the x-ray source 105, the collimator module 106, the x-ray beam limiter assembly 108, an x-ray beam emitter, and an external reference point. For example, in an embodiment, during operation, the x-ray collimator module 106 is configured to adjust the x-ray beam field size responsive to one or more inputs from the x-ray collimator module 106 indicative of an intra-oral x-ray sensor border position. In an embodiment, during operation, the x-ray collimator module 106 is configured to adjust the x-ray beam field size responsive to one or more inputs from the x-ray collimator module 106 indicative of an intra-oral x-ray sensor centroid 126 position. In an embodiment, during operation, the x-ray collimator module 106 is configured to adjust the x-ray beam field size responsive to one or more inputs from the x-ray collimator module 106 indicative of an intra-oral x-ray sensor angular orientation.

In an embodiment, the x-ray collimator module 106 is configured to adjust the x-ray beam field size responsive to one or more inputs from the x-ray collimator module 106 indicative of an intra-oral x-ray sensor dimension. In an embodiment, the x-ray collimator module 106 is configured to generate one or more parameters associated with an x-ray beam limiter assembly 108 configuration responsive to one or more inputs from an intra-oral x-ray sensor 102.

In an embodiment, the x-ray collimator module 106 is configured to generate at least one parameter associated with an x-ray imaging mode (e.g., adult panoramic mode, child panoramic mode, high-dose-rate mode, low-dose-rate mode, moderate-dose-rate mode mandible mode, occlusion mode, maxillary mode, panoramic mode, pulsed fluoroscopy mode, temporomandibular joint mode, etc.) responsive to one or more inputs from an intra-oral x-ray sensor 102. In an embodiment, the intra-oral x-ray imaging system 100 includes a field of view module 107 operable to generate one or more parameters associated with a field of view setting (e.g., field of view size, field of view shape, wide field of view, narrow field of view, field of view extension, horizontal field of view, vertical field of view, diagonal field of view, magnification, increase, decrease, etc.) responsive to one or more inputs from the x-ray collimator module 106 indicative of an intra-oral x-ray sensor position, orientation, or the like.

In an embodiment, the intra-oral x-ray imaging system 100 includes one or more intra-oral x-ray sensors 102 configured to acquire intra-oral x-ray image information 104 associated with a patient. In an embodiment, the intra-oral x-ray imaging system 100 includes an x-ray image component 116 operably coupled to one or more intra-oral x-ray sensors 102.

Non-limiting examples of intra-oral x-ray sensors 102 include film-based analog x-ray sensors, dental digital x-ray sensors, charge-coupled device (CCD) sensors, complementary metal-oxide-semiconductor (CMOS) sensors, and the like. In an embodiment, the intra-oral x-ray imaging system 100 includes one or more intra-oral x-ray sensors 102 having at least one scintillator plate. In an embodiment, the intra-oral x-ray imaging system 100 includes one or more intra-oral x-ray sensors 102 having at least one scintillator layer. In an embodiment, a scintillator layer is vapor-deposited onto an optical fiber coupled to a photo-sensor integrated into a CCD or CMOS chip. Further non-limiting examples of intra-oral x-ray sensors 102 includes scintillators (e.g., inorganic scintillators, thallium doped cesium iodide scintillators, scintillator-photodiode pairs, scintillation detection devices, etc.), dosimeters (e.g., x-ray dosimeters, thermoluminescent dosimeters, etc.), optically stimulated luminescence detectors, photodiode arrays, charge-coupled devices (CCDs), complementary metal-oxide-semiconductor (CMOS) devices, or the like.

In an embodiment, the intra-oral x-ray sensor 102 includes one or more transducers that detect and convert x-rays into electronic signals. For example, in an embodiment, the intra-oral x-ray sensor 102 includes one or more x-ray radiation scintillation crystals. In an embodiment, the intra-oral x-ray sensor 102 includes one or more thallium doped cesium iodide crystals (e.g., cesium iodide crystals doped with thallium CsI(Tl)). In an embodiment, during operation the intra-oral x-ray sensor 102 includes a computing device that processes the electronic signals generated by the one or more transducers to determine one or more of intensity, energy, time of exposure, date of exposure, exposure duration, rate of energy deposition, depth of energy deposition, and the like associated with each x-ray detected. In an embodiment, during operation, incident x-ray radiation interacts with one or more detector crystalline materials (e.g., cadmium zinc telluride, etc.) within the intra-oral x-ray sensor 102, which results in the generation of a current indicative of, for example, the energy of the incident x-ray radiation.

In an embodiment, the intra-oral x-ray sensor 102 includes an amorphous-carbon substrate coupled to a Cesium Iodide (CsI) scintillator. In an embodiment, the intra-oral x-ray sensor 102 includes a fiber optic plate (FOP) coupled to a CsI scintillator. In an embodiment, the intra-oral x-ray sensor 102 includes an aluminum substrate coupled to a CsI scintillator. In an embodiment, the intra-oral x-ray sensor 102 includes a scintillator configured to reduce scattering. For example, in an embodiment, the intra-oral x-ray sensors 102 includes thallium-doped-Cesium Iodide (CsI:Tl) having columnar structure deposited on a substrate operably coupled to a CMOS/CCD sensor. See e.g., Zhao et al. *X-ray imaging performance of structured cesium iodide scintillators.* Med. Phys. 31, 2594-2605 (2004) which is incorporated herein by reference. The columnar structure of CsI helps to selectively pass a portion of the x-ray bean onto a CMOS/CCD sensor forming part of the intra-oral x-ray sensor 102.

In an embodiment, the intra-oral x-ray sensor 102 includes a substrate that acquires at least a portion of penetrating x-ray radiation stimulus and transduces the penetrating x-ray radiation stimulus acquired by the intra-oral x-ray sensor 102 into an image or at least one measurand indicative of an x-ray flux throughput during an integration period of the intra-oral x-ray sensor 102.

In an embodiment, an x-ray image component 116 component is operably coupled to an intra-oral x-ray sensor 102 having one or more x-ray radiation fluoroscopic elements. In an embodiment, the intra-oral x-ray sensor 102 includes one or more phosphorus doped elements (e.g., ZnCdS:Ag phosphorus doped elements). In an embodiment, the intra-oral x-ray sensor 102 includes one or more amorphous silicon thin-film transistor arrays. In an embodiment, the intra-oral x-ray sensor 102 includes one or more phosphors.

In an embodiment, the x-ray image component 116 is operably coupled to one or more active pixel image sensors. In an embodiment, the x-ray image component 116 is operably coupled to one or more complementary metal-oxide-semiconductor sensors. In an embodiment, the x-ray image component 116 is operably coupled to one or more complementary metal-oxide-semiconductor active pixel sensors.

In an embodiment, the intra-oral x-ray imaging system 100 includes at least one intra-oral x-ray sensor 102 wirelessly coupled to the x-ray collimator module 106. In an embodiment, the intra-oral x-ray imaging system 100 includes at least one intra-oral x-ray sensor 102 wired or wirelessly coupled to an x-ray source 105.

In an embodiment, the intra-oral x-ray imaging system 100 includes an intra-oral x-ray sensor module 109 operably coupled to the intra-oral x-ray sensor 102 and the x-ray collimator module. In an embodiment, the intra-oral x-ray sensor module 109 is configured to generate one or more of intra-oral x-ray sensor dimension information, intra-oral x-ray sensor orientation information, or intra-oral x-ray sensor position information responsive to one or more inputs from the x-ray image sensor 102 or the x-ray collimator module 106. In an embodiment, the x-ray collimator module 106 is in wireless communication with the intra-oral x-ray sensor module.

In an embodiment, during operation, the intra-oral x-ray imaging system 100 is configured to determine the position and orientation of the intra-oral x-ray sensor 102, and to adjust an x-ray beam field of view responsive to determining the position and orientation of the intra-oral x-ray sensor 102. For example, in an embodiment, the intra-oral x-ray imaging system 100 includes a camera, a sensor, a component, etc., configured to acquire image information associated with a position or an orientation of the intra-oral x-ray sensor 102. In an embodiment, the camera acquires an image involving one or more beacons 118, phosphors 120, retroreflectors 122, or the like that are configured to indicate the position or orientation of the intra-oral x-ray sensor 102.

In an embodiment, the x-ray collimator module 106 is operably coupled to one or more sensors, components, etc., configured to determine, indicate, communicate, broadcast, etc., a border position of the intra-oral sensor 102. In an embodiment, the x-ray collimator module 106 is operably coupled to one or more beacons 118, phosphors 120, retroreflectors 122, or the like configured to determine, indicate, communicate, broadcast, etc., a border position of the intra-oral sensor 102. For example, during operation, the x-ray collimator module 106 is configured to acquire one or more inputs from one or more beacons 118 indicative of the position or orientation of the intra-oral x-ray sensor 102. In an embodiment, during operation, the x-ray collimator module 106 is configured to acquire one or more electrical, acoustic, or electromagnetic inputs from one or more beacons 118 indicative of the position or orientation of the intra-oral x-ray sensor 102.

In an embodiment, during operation, the x-ray collimator module 106 is configured to acquire one or more inputs from a sensor configure to detect a florescence associated with one or more phosphors 120, and to generate information indicative of the position or orientation of the intra-oral x-ray sensor 102 based on the one or more inputs from the sensor. In an embodiment, the x-ray collimator module 106 is operably coupled to one or more sensors configured to generate one or more outputs indicative of the position or orientation of the intra-oral x-ray sensor 102. In an embodiment, the x-ray collimator module 106 is operably coupled to one or retroreflectors configured to indicate the position or orientation of the intra-oral x-ray sensor 102.

In an embodiment, the x-ray collimator module 106 is operably coupled to one or more beacons 118 configured to indicate, communicate, convey, etc., position information or orientation information associated with an intra-oral x-ray sensor 102. Non-limiting examples of beacons 118 include infrared emitters, ultraviolet emitters, visible emitters, electromagnetic energy emitters, ultrasound emitters, and the like. Further non-limiting examples of beacons 118 include magnetic field generators, inductors, capacitors, or the like. In an embodiment, during operation, the x-ray collimator module 106 adjusts an x-ray beam field of view responsive to detecting one or more emitted signals from a beacon 118. In an embodiment, the x-ray collimator module 106 is operably coupled to one or more beacons 118 configured to emit an ultrasonic output. In an embodiment, the x-ray collimator module 106 is operably coupled to one or more beacons 118 configured to emit an ultrasonic output that is detectable through tissue.

In an embodiment, the x-ray collimator module 106 is operably coupled to one or more phosphors 120 configured to indicate the position or orientation of the intra-oral x-ray sensor 102. Non-limiting examples of phosphors 120 include infrared phosphors, ultraviolet phosphors, visible phosphors, x-ray phosphors, and the like. Further non-limiting examples of phosphors 120 include phosphors having a peak emission wavelength associated with an optical window in biological tissue. See e.g. J. Phys. D: Appl. Phys. 46 (2013) 375401 (5 pp) which is incorporated herein by reference. In an embodiment, the x-ray collimator module 106 is operably coupled to one or more phosphors 120 configured to provide a signal through the patient's skin (i.e. cheek, gum, or teeth). In an embodiment, the x-ray collimator module 106 is operably coupled to one or more phosphors 120 having a peak emission wavelength ranging from about 650 nanometers to about 900 nanometers. In an embodiment, during operation, the border position of the intra-oral sensor 102 is signaled by one or more phosphors 120. In an embodiment, during operation, the x-ray collimator module 106 adjusts an x-ray beam field of view responsive to detecting one or more phosphors 120 and determining a border position of the intra-oral sensor 102 based on determining the location of the one or more phosphors 120.

In an embodiment, the intra-oral x-ray sensor comprises a position sensor 124 configured to determine border position data, and a transmitter configured to transmit a signal indicative of the border position data. In an embodiment, the border position data includes X, Y, and Z coordinates. In an embodiment, the border position data includes one or more parameters that define a specific location in a two-dimensional object or three-dimensional object. In an embodiment, the border position data includes one or more position parameters associated with an intra-oral x-ray sensor border. In an embodiment, the border position data includes one or more position parameters associated with an intra-oral x-ray sensor centroid 126. Non-limiting examples of position sensors 124 include local positioning system (e.g., analogous to GPS-type sensors) sensors configured to interact with room-based reference signals. In an embodiment, the position sensor 124 includes a magnetic sensor responding to room-based magnetic fields. In an embodiment, the position sensor 124 includes one or more accelerometer 128. In an embodiment, the position sensor 124 includes a multi-accelerometer or accelerometer-gyro package that keeps track of the motion involved in putting intra-oral x-ray sensor 102 into the patient's mouth.

In an embodiment, the x-ray collimator module 106 is configured to adjust the x-ray beam to minimize the portion of the x-ray beam that misses (e.g., overfills) the intra-oral x-ray sensor 102. In an embodiment, the x-ray collimator module 106 is further configured to adjust the x-ray beam to maximize an amount of the x-ray beam that impacts the intra-oral x-ray sensor 102, e.g., to minimize underfilling it.

Figure 2A:
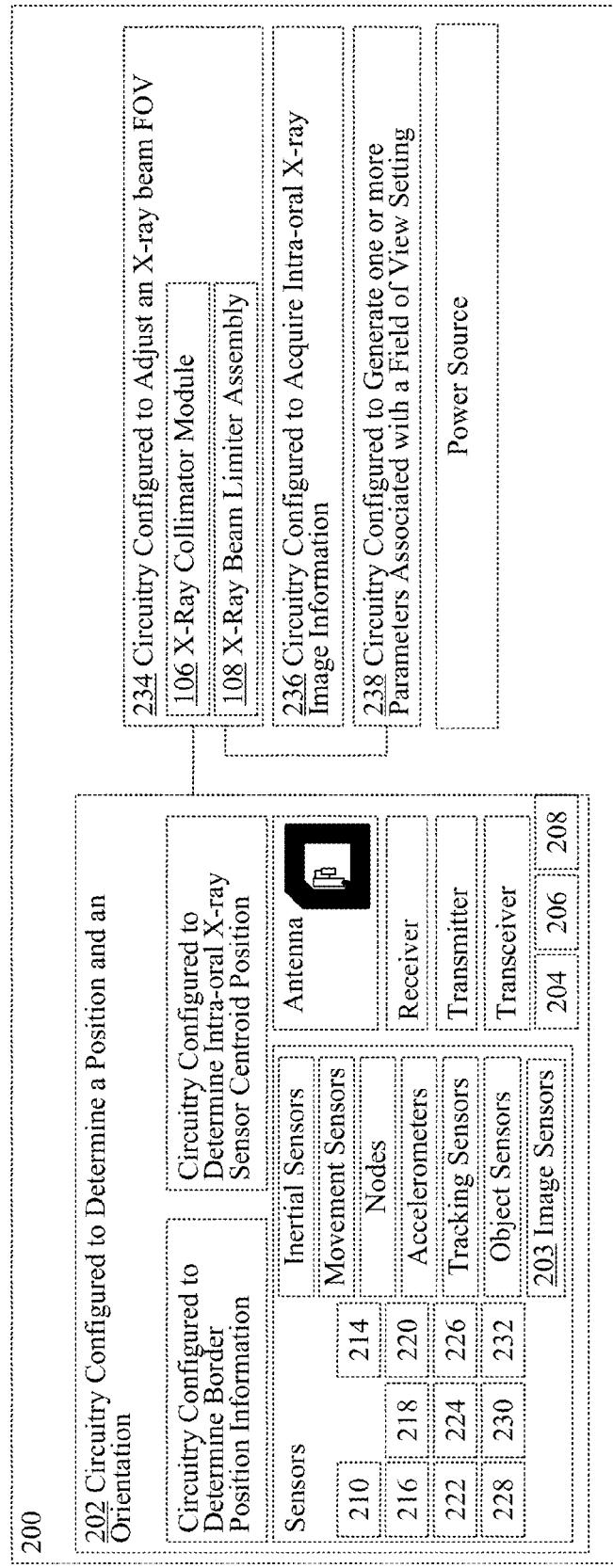
FIG. 2A is a perspective view of an intra-oral x-ray imaging system according to one embodiment.
Figure 2B:
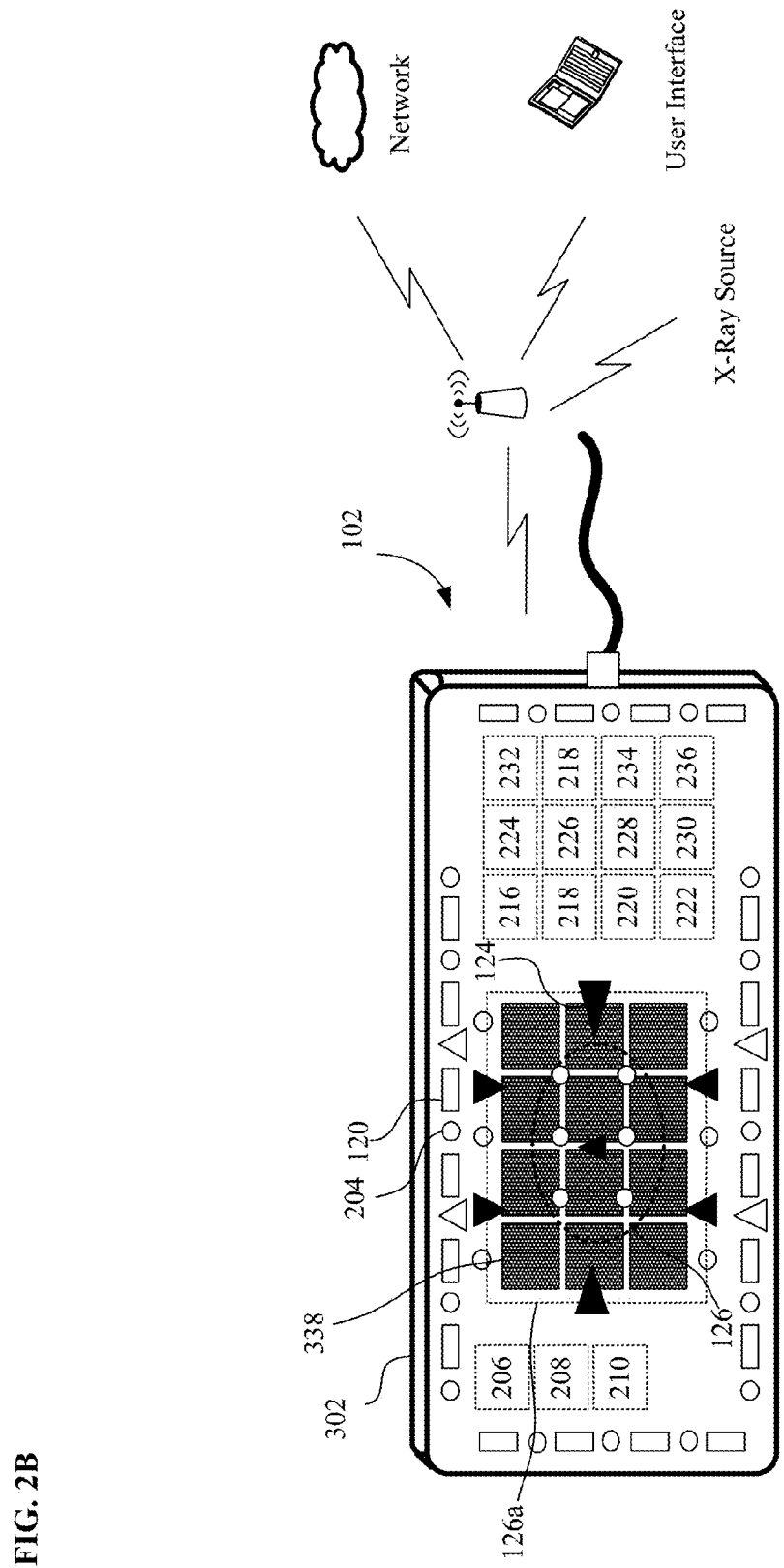
FIG. 2B is a perspective view of an intra-oral x-ray system according to one embodiment.

FIG. 2A shows an intra-oral x-ray imaging device 200 in which one or more methodologies or technologies can be implemented such as, for example, reducing patient exposure to x-rays, reducing amount of scatter, transmission, or re-radiation during imaging, or improving x-ray image quality. In an embodiment, the intra-oral x-ray imaging device 200 includes circuitry 202 configured to determine a position and an orientation of an intra-oral x-ray sensor 102. In an embodiment, the circuitry 202 configured to determine the position and the orientation of the intra-oral x-ray sensor 102 includes circuitry configured to determine border position information of the intra-oral x-ray sensor 102. In an embodiment, the circuitry 202 configured to determine the position and the orientation of the intra-oral x-ray sensor 102 includes circuitry configured to determine an intra-oral x-ray sensor centroid position.

In an embodiment, the circuitry 202 configured to determine the position and the orientation of the intra-oral x-ray sensor 102 includes an image sensor 203 configured to detect one or more optic devices 204 (e.g., retroreflectors, beacons, emitters, etc.) indicative of an intra-oral x-ray sensor border position, an intra-oral x-ray sensor position, or an intra-oral x-ray sensor orientation. In an embodiment, the circuitry 202 configured to determine the position and the orientation of the intra-oral x-ray sensor 102 is operably coupled to an embedded orientation detection component 206. In an embodiment, the circuitry 202 configured to determine the position and the orientation of the intra-oral x-ray sensor 102 and the one or more acoustic transducers 232 form part of an integrated component.

In an embodiment, the circuitry 202 configured to determine the position and the orientation of the intra-oral x-ray sensor 102 is operably coupled to one or more magnetic compass based sensors 208. For example, in an embodiment, the circuitry 202 configured to determine the position and the orientation of the intra-oral x-ray sensor 102 is operably coupled to one or more embedded magnetic compass sensors 210. In an embodiment, the circuitry 202 configured to determine position and the orientation of the intra-oral x-ray sensor 102 and the one or more embedded magnetic compass sensors 210 form part of an integrated component.

In an embodiment, the circuitry 202 configured to determine the position and the orientation of the intra-oral x-ray sensor 102 forms part of an integrated image sensor configured to detect one or more optic devices 204 (e.g., retroreflectors, beacons, emitters, etc.)

In an embodiment, the circuitry 202 configured to determine the position and the orientation of the intra-oral x-ray sensor 102 is operably coupled to one or more local positioning system based sensors 124. In an embodiment, the circuitry 202 configured to determine the position and the orientation of the intra-oral x-ray sensor 102 is operably coupled to one or more acceleration sensors 214. In an embodiment, the circuitry 202 configured to determine the position and the orientation of the intra-oral x-ray sensor 102 is operably coupled to at least two acceleration sensors 214 in a substantially perpendicularly arrangement. In an embodiment, the circuitry 202 configured to determine the position and the orientation of the intra-oral x-ray sensor 102 is operably coupled to one or more multi-axis accelerometers 216.

In an embodiment, the circuitry 202 configured to determine the position and the orientation of the intra-oral x-ray sensor 102 is operably coupled to one or more orientation-aware sensors 218. For example, in an embodiment, the circuitry 202 configured to determine the position and the orientation of the intra-oral x-ray sensor is operably coupled to one or more gyroscopes 220. In an embodiment, the circuitry 202 configured to determine the position and the orientation of the intra-oral x-ray sensor 102 is operably coupled to one or more electrolytic fluid based sensors 222.

In an embodiment, the circuitry 202 configured to determine the position and the orientation of the intra-oral x-ray sensor 102 is operably coupled to a two-axis tilt sensor 224 configured to detect an intra-oral x-ray sensor roll or yaw angle. In an embodiment, the circuitry 202 configured to determine the position and the orientation of the intra-oral x-ray sensor 102 is operably coupled to a two-axis tilt sensor 224 configured to detect an intra-oral x-ray sensor pitch angle.

In an embodiment, the circuitry 202 configured to determine the position and the orientation of the intra-oral x-ray sensor 102 is operably coupled to one or more inductors 226. In an embodiment, the circuitry 202 configured to determine the position and the orientation of the intra-oral x-ray sensor 102 is operably coupled to one or more active optic devices 228. For example, in an embodiment, the circuitry 202 configured to determine the position and the orientation of the intra-oral x-ray sensor 102 is operably coupled to one or more optical emitter that emit an electromagnetic energy signal that provides information associated with the position and the orientation of the intra-oral x-ray sensor 102. In an embodiment, the circuitry 202 configured to determine the position and the orientation of the intra-oral x-ray sensor 102 is operably coupled to one or more active acoustic emitters.

In an embodiment, the circuitry 202 configured to determine the position and the orientation of the intra-oral x-ray sensor 102 is operably coupled to one or more passive optics devices 230 (e.g., retroreflectors, phosphors, etc.). In an embodiment, during operation, the circuitry 202 configured to determine the position and the orientation of the intra-oral x-ray sensor 102 by emitting an interrogation signal that is reflected back by the one or more retroreflectors. The reflected signal is use to generate information associated with the position and the orientation of the intra-oral x-ray sensor 102.

In an embodiment, the circuitry 202 configured to determine the position and the orientation of the intra-oral x-ray sensor 102 is operably coupled to one or more acoustic transducers 232 configured to generate an output indicative of an intra-oral x-ray sensor border position and an intra-oral x-ray sensor orientation. In an embodiment, the circuitry 202 configured to determine the position and the orientation of the intra-oral x-ray sensor 102 and the one or more acoustic transducers 232 form part of an integrated component.

In an embodiment, the intra-oral x-ray sensor 102 includes an integrated component including one or more optic devices 204, orientation detection component 206, magnetic compass based sensors 208, embedded magnetic compass sensors 210, local positioning system based sensors 124, more acceleration sensors 214, multi-axis accelerometers 216, orientation-aware sensors 218, gyroscopes 220, electrolytic fluid based sensors 222, two-axis tilt sensors 224, inductors 226, optic devices 228, passive optics devices 230, acoustic transducers 232, or the like.

In an embodiment, the intra-oral x-ray imaging device 200 includes circuitry 234 configured to adjust an x-ray beam field of view (FOV) responsive to one or more inputs from the circuitry 202 configured to determine the position and the orientation of the intra-oral x-ray sensor 102. For example, in an embodiment, the circuitry 234 configured to adjust the x-ray beam field of view is operably coupled to at least one of the x-ray collimator module 106 or the x-ray beam limiter assembly 108, and is configured to generate one or more control signal that actuates the x-ray collimator module 106 or the x-ray beam limiter assembly 108 to adjust an x-ray beam FOV responsive to one or more inputs from the circuitry 202 configured to determine the position and the orientation of the intra-oral x-ray sensor 102.

In an embodiment, the intra-oral x-ray imaging device 200 includes circuitry 236 configured to acquire intra-oral x-ray image information associated with a patient. In an embodiment, the intra-oral x-ray imaging device 200 includes circuitry 238 configured to generate one or more parameters associated with a field of view setting. In an embodiment, the circuitry 238 configured to generate one or more parameters associated with a field of view setting includes circuitry configured to generate the one or more parameters associated with the field of view setting responsive to one or more inputs from the circuitry 202 configured to determine the position and the orientation of the intra-oral x-ray sensor 102.

Figure 3A:
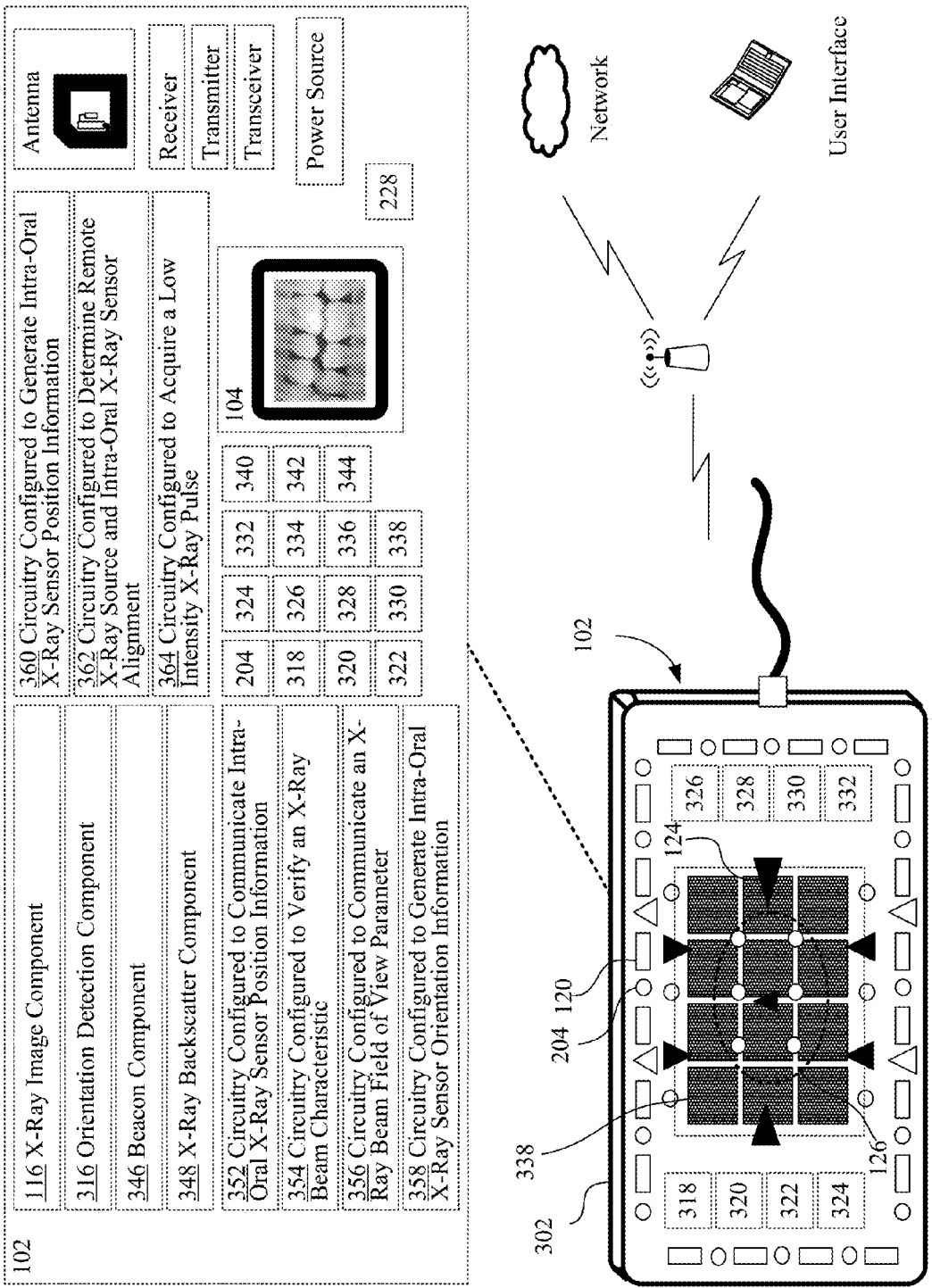
FIG. 3A is a perspective view of an intra-oral x-ray sensor according to one embodiment.

FIG. 3A shows an intra-oral x-ray sensor 102 in which one or more methodologies or technologies can be implemented such as, for example, reducing patient exposure to x-rays, reducing amount of scatter, transmission, or re-radiation during imaging, or improving x-ray image quality. In an embodiment, the intra-oral x-ray sensor 102 includes an x-ray image component 116 configured to acquire intra-oral x-ray image information 104 associated with a patient. In an embodiment, the x-ray image component 116 includes circuitry 236 configured to acquire intra-oral x-ray image information associated with a patient. In an embodiment, the intra-oral x-ray sensor 102 includes an intra-oral radiation shield structure 302 configured to reduce at least one of x-ray scattering, transmission, or re-radiation by at least 50%.

In an embodiment, the intra-oral radiation shield structure 302 includes one or more high atomic number (high-Z) materials in an amount sufficient to reduce at least one of x-ray scattering, transmission, or re-radiation by at least 50%. For example, in an embodiment, at least a portion of the intra-oral radiation shield structure 302 is formed from materials including elements have an atomic number greater than or equal to 37 (Rubidium or higher). In an embodiment, at least a portion of the intra-oral radiation shield structure 302 is formed from materials including elements have an atomic number greater than or equal to 72 (Hathium or higher).

In an embodiment, the intra-oral radiation shield structure 302 includes one or more materials having a K-edge greater than 15 kiloelectron volts in an amount sufficient to reduce at least one of x-ray scattering, transmission, or re-radiation by at least 50%. Non-limiting examples of materials having a K-edge greater than 15 kiloelectron volts include elements have an atomic number greater than or equal to 37 (Rubidium or higher). In an embodiment, the intra-oral radiation shield structure 302 includes one or more materials having an L-edge greater than 10 kiloelectron volts in an amount sufficient to reduce at least one of x-ray scattering, transmission, or re-radiation by at least 50%. Non-limiting examples of materials having an L-edge greater than 10 kiloelectron volts include elements have an atomic number greater than or equal to 69 (Thulium or higher).

In an embodiment, the intra-oral radiation shield structure 302 includes a mixture of materials having a K-edge greater than 15 kiloelectron volts, materials having an L-edge greater than 10 kiloelectron volts, or high atomic number (high-Z) materials in an amount sufficient to reduce at least one of x-ray scattering, transmission, or re-radiation by at least 50%.

Figure 3B:
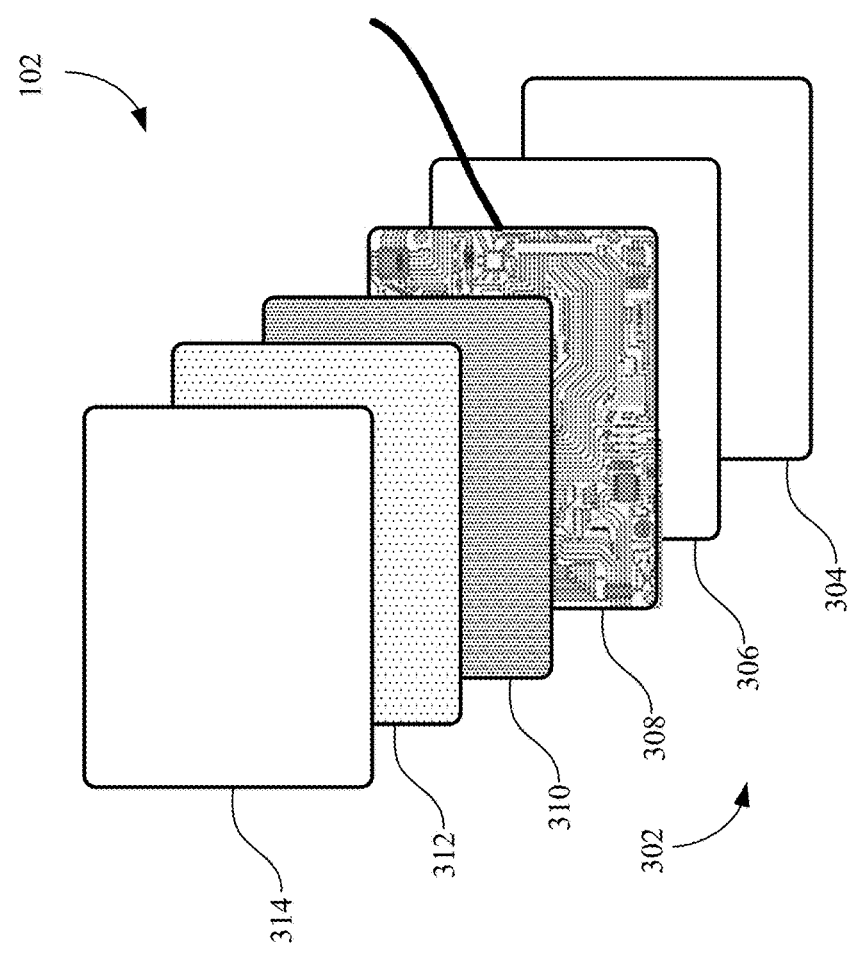
FIG. 3B is a perspective view of an intra-oral x-ray sensor according to one embodiment.

Referring to FIG. 3B, in an embodiment, the intra-oral x-ray sensor 102 includes a laminate structure having multiple layers. For example, in an embodiment, the intra-oral x-ray sensor 102 includes one or more of radiation shield layers 304, 306, electronic circuit layers 308, sensor layers 310, scintillator layers 312, protection layers 314, etc. In an embodiment, the intra-oral radiation shield structure 302 includes a laminate structure having at least a first layer 304. In an embodiment, the intra-oral radiation shield structure 302 includes a laminate structure having at least a first layer 304 and a second layer 306, the second layer having an x-ray attenuation profile different from the first layer. In an embodiment, the intra-oral radiation shield structure 302 includes a laminate structure having at least a first layer 304 and a second layer 306, the second layer 306 having an attenuation coefficient different from the first layer 304.

In an embodiment, at least a portion of the intra-oral radiation shield structure 302 is composed of one or more x-ray shielding materials. In an embodiment, at least a portion of the intra-oral radiation shield structure 302 is composed of one or more x-ray radio-opaque materials (e.g., barium sulfate, silicon carbide, silicon nitride, alumina, zirconia, etc.). In an embodiment, at least a portion of the intra-oral radiation shield structure 302 is composed of one or more x-ray attenuating materials. In an embodiment, at least a portion of the intra-oral radiation shield structure 302 is composed of one or more x-ray attenuating ceramic materials. In an embodiment, at least a portion of the intra-oral radiation shield structure 302 is composed of multiple layers, each layer having an xx-ray attenuation coefficient different from another.

In an embodiment, at least a portion of the intra-oral radiation shield structure 302 is composed of one or more ferromagnetic materials. Ferromagnetic materials include those materials having a Curie temperature, above which thermal agitation destroys the magnetic coupling giving rise to the alignment of the elementary magnets (electron spins) of adjacent atoms in a lattice (e.g., a crystal lattice). In an embodiment, one or more of the plurality of x-ray shielding particles include one or more ferromagnets. Non-limiting examples ferromagnetic materials include crystalline ferromagnetic materials, ferromagnetic oxides, materials having a net magnetic moment, materials having a positive susceptibility to an external magnetic field, non-conductive ferromagnetic materials, non-conductive ferromagnetic oxides, ferromagnetic elements (e.g., cobalt, gadolinium, iron, or the like), rare earth elements, ferromagnetic metals, ferromagnetic transition metals, materials that exhibit magnetic hysteresis, and the like, and alloys or mixtures thereof.

Further non-limiting examples of ferromagnetic materials include chromium (Cr), cobalt (Co), copper (Cu), dysprosium (Dy), europium (Eu), gadolinium (Gd), iron (Fe), magnesium (Mg), neodymium (Nd), nickel (Ni), yttrium (Y), and the like. Further non-limiting examples of ferromagnetic materials include chromium dioxide ($CrO_2$), copper ferrite ($CuOFe_2O_3$), europium oxide (EuO), iron(II, III) oxide ($FeOFe_2O_3$), iron(III) oxide ($Fe_2O_3$), magnesium ferrite ($MgOFe_2O_3$), manganese ferrite ($MnOFe_2O_3$), nickel ferrite ($NiOFe_2O_3$), yttrium-iron-garnet ($Y_3Fe_5O_{12}$), and the like. Further non-limiting examples of ferromagnetic materials include manganese arsenide (MnAs), manganese bismuth (MnBi), manganese (III) antimonide (MnSb), Mn—Zn ferrite, neodymium alloys, neodymium, Ni—Zn ferrite, and samarium-cobalt.

In an embodiment, at least a portion of the intra-oral radiation shield structure 302 is composed of iron oxides. Non-limiting examples of iron oxides include copper ferrite ($CuOFe_2O_3$), iron(II, III) oxide ($FeOFe_2O_3$), iron(III) oxide ($Fe_2O_3$), magnesium ferrite ($MgOFe_2O_3$), manganese ferrite ($MnOFe_2O_3$), nickel ferrite ($NiOFe_2O_3$), yttrium-iron-garnet ($Y_3Fe_5O_{12}$), ferric oxides, ferrous oxides, and the like. In an embodiment, one or more of the plurality of x-ray shielding particles include at least one iron oxide.

In an embodiment, at least a portion of the intra-oral radiation shield structure 302 is composed of one or ferrimagnetic materials. In an embodiment, one or more of the plurality of x-ray shielding particles include one or more ferrimagnets (e.g., soft ferrites, hard ferrites, or the like). Non-limiting examples of ferrimagnetic materials include ferrimagnetic oxides (e.g., ferrites, garnets, or the like). Further non-limiting examples of ferrimagnetic materials include ferrites with a general chemical formula of $AB_2O_4$ (e.g., $CoFe_2O_4$, $MgFe_2O_4$, $ZnFe_2O_4$) where A and B represent various metal cations. In an embodiment, A is Mg, Zn, Mn, Ni, Co, or Fe(II); B is Al, Cr(III), Mn(III) or Fe(III), and O is oxygen. In an embodiment, A is a divalent atom of radius ranging from about 80 pm to about 110 pm (e.g., Cu, Fe, Mg, Mn, Zn, or the like), B is a trivalent atom of radius ranging from about 75 pm to about 90 pm, (e.g., Al, Fe, Co, Ti, or the like), and O is oxygen. Non-limiting examples of ferrimagnetic materials include iron ferrites with a general chemical formula $MOFe_2O_3$ (e.g., $CoFe_2O_4$, $Fe_3O_4$, $MgFe_2O_4$, or the like) where M is a divalent ion such as Fe, Co, Cu, Li, Mg, Ni, or Zn. In an embodiment, at least a portion of the intra-oral radiation shield structure 302 is composed of at least a first ferrimagnetic material and a second ferrimagnetic material, the second ferrimagnetic material having one or more absorption edges different from the first ferrimagnetic material. In an embodiment, the intra-oral radiation shield structure 302 includes a laminate structure having at least a first layer 304 and a second layer 306, the second layer having a different ferrimagnetic material composition from the first layer.

Non-limiting examples of ferrimagnetic materials include materials having a magnetization compensation point, materials that are associated with a partial cancellation of anti-ferromagnetically aligned magnetic sublattices with different values of magnetic moments, or material having different temperature dependencies of magnetization. See e.g., Kageyama et al., Weak Ferrimagnetism, Compensation Point, and Magnetization Reversal in $Ni(HCOO)_2.2H_2O$, Physical Rev. B, 224422 (2003). In an embodiment, at least a portion of the intra-oral radiation shield structure 302 comprises one or more paramagnetic materials.

In an embodiment, the intra-oral radiation shield structure 302 is removably attachable to the intra-oral x-ray sensor 102. For example, in an embodiment, at least a portion of the intra-oral radiation shield structure 302 is removably attachable to the intra-oral x-ray sensor 102, behind a sensor layer 310. In an embodiment, at least a portion of the intra-oral radiation shield structure 302 includes two or more layers secured to each other to form structure 302.

In an embodiment, at least a portion of the intra-oral radiation shield structure 302 is composed of one or more x-ray radio-opaque materials. In an embodiment, at least a portion of the intra-oral radiation shield structure 302 is composed of one or more x-ray attenuating materials. In an embodiment, at least a portion of the intra-oral radiation shield structure 302 is composed of one or more x-ray attenuating ceramic materials.

In an embodiment, at least a portion of the intra-oral radiation shield structure 302 is composed of at least a first x-ray radio-opaque material and a second x-ray radio-opaque material, the second x-ray radio-opaque material having a different x-ray opacity profile from the first x-ray radio-opaque material. In an embodiment, the intra-oral radiation shield structure 302 includes a laminate structure having at least a first layer 304 and a second layer 306, the second layer 306 having a different opacity profile from the first layer 304.

In an embodiment, at least a portion of the intra-oral radiation shield structure 302 is formed from at least one x-ray attenuating material, x-ray radio-opaque material, or x-ray attenuating ceramic material. In an embodiment, at least a portion of the intra-oral radiation shield structure 302 is formed from at least one ferromagnetic material, ferrimagnetic material, or paramagnetic material. In an embodiment, at least a portion of the intra-oral radiation shield structure 302 is composed of one or more high-Z, high-density, materials.

In an embodiment, at least a portion of the intra-oral radiation shield structure 302 is composed of at least a first x-ray attenuating ceramic material and a second x-ray attenuating ceramic material, the second x-ray attenuating ceramic material having a different x-ray attenuation profile from the first x-ray attenuating ceramic material. In an embodiment, the intra-oral radiation shield structure 302 includes a laminate structure having at least a first layer 304 and a second layer 306, the second layer 306 having a different x-ray attenuation profile from the first layer 304.

In an embodiment, at least a portion of the intra-oral radiation shield structure 302 is composed of at least a first x-ray shielding material and a second x-ray shielding material, the second x-ray shielding material having one or more absorption edges different from the first x-ray shielding material. In an embodiment, at least one of the first x-ray shielding material or the second x-ray shielding material includes at least one material that absorbs x-rays at one or more frequencies and fluoresce x-rays at one or more lower frequencies. In an embodiment, at least one absorption edge of the second x-ray shielding material is selected to maximize absorption of x-rays fluoresced by the first x-ray shielding material. In an embodiment, at least a portion of the second x-ray shielding material is mounted between an x-ray image detector and a portion of the first x-ray shielding material on the intra-oral x-ray sensor 102. In an embodiment, at least a portion of the second x-ray shielding material is intermixed with at least a portion of the first x-ray shielding material. In an embodiment, at least a portion of the second x-ray shielding material is interlayered with at least a portion of the first x-ray shielding material.

In an embodiment, at least a portion of the intra-oral radiation shield structure 302 is composed of at least a first x-ray shielding material and a second x-ray shielding material, the second x-ray shielding material having a different absorption edge profile from the first x-ray shielding material. In an embodiment, the intra-oral radiation shield structure 302 includes a laminate structure having at least a first layer 304 and a second layer 306, the second layer 306 having a different x-ray absorption edge profile from the first layer 304.

In an embodiment, the second x-ray shielding material includes one or more K-edges, or one or more L-edges, different from the first x-ray shielding material. In an embodiment, the second x-ray shielding material includes at least one K-edge having an energy level lower than at least one K-edge of the first x-ray shielding material. In an embodiment, at least one of the first x-ray shielding material or the second x-ray shielding material includes at least one of lead (Pb), tantalum (Ta), or tungsten (W). In an embodiment, the second x-ray shielding material comprises an x-ray mass attenuation coefficient different from the first x-ray shielding material.

In an embodiment, the intra-oral radiation shield structure 302 includes one or more x-ray shielding agents. For example, in an embodiment, the intra-oral radiation shield structure 302 includes a composition having a carrier fluid and a plurality of x-ray shielding particles each having at least a first x-ray shielding agent and a second x-ray shielding agent, the second x-ray shielding agent having one or more absorption edges different from the first x-ray shielding agent. In an embodiment, the intra-oral radiation shield structure 302 includes at least a first x-ray shielding agent and a second x-ray shielding agent, the second x-ray shielding agent having one or more absorption edges different from the first x-ray shielding agent.

In an embodiment, the intra-oral radiation shield structure 302 includes at least a first x-ray shielding agent and a second x-ray shielding agent. In an embodiment, at least one of the first x-ray shielding agent or the second x-ray shielding agent includes at least one of mercury (Hg), lead (Pb), tantalum (Ta), or tungsten (W). In an embodiment, at least one of the first x-ray shielding agent or the second x-ray shielding agent includes at least one of teflon ($C_2F_4$), lead (II) oxide (PbO), or silicon nitride ($Si_3N_4$). In an embodiment, at least one of the first x-ray shielding agent or the second x-ray shielding agent includes at least one of boron, molybdenum, neodymium, niobium, strontium, tungsten yttrium, or zirconium, or combinations thereof. In an embodiment, at least one of the first x-ray shielding agent or the second x-ray shielding agent includes at least one of barium sulfate ($BaSO_4$), boron nitride (BN), boron carbide ($B_4C$), boron oxide ($B_2O_3$), or barium oxide (BaO). In an embodiment, at least one of the first x-ray shielding agent or the second x-ray shielding agent includes at least one of strontium oxide (SrO), zinc oxide (ZnO), or zirconium dioxide ($ZrO_2$).

In an embodiment, at least one of the first x-ray shielding agent or the second x-ray shielding agent includes at least one of $SiO_2$—PbO-alkali metal oxide glass, CaO—SrO—$B_2O_3$ glass, or boron-lithium glass. In an embodiment, at least one of the first x-ray shielding agent or the second x-ray shielding agent includes borated high density polyethylene. In an embodiment, at least one of the first x-ray shielding agent or the second x-ray shielding agent includes at least one of mylar ($C_{10}H_8O_4$), parylene-C ($C_8H_7Cl$), parylene-N ($C_8H_8$), poly(methyl methacrylate) (PMMA), polycarbonate ($C_{16}H_4O_3$), polyethylene, or ultra-high molecular weight polyethylene.

In an embodiment, a portion of the intra-oral radiation shield structure 302 is configured to have an x-ray shielding lead equivalence of about 0.25 millimeters to about 0.5 millimeters. For example, in an embodiment, a portion of the intra-oral radiation shield structure 302 includes a sufficient amount of x-ray shielding materials to have an x-ray shielding lead equivalence of about 0.25 millimeters to about 0.5 millimeters. In an embodiment, x-ray shielding lead equivalence is configured based on an anticipated x-ray spectrum. In an embodiment, a portion of the intra-oral radiation shield structure 302 has an x-ray shielding lead equivalence of greater than about 0.25 millimeters.

In an embodiment, a portion of the intra-oral radiation shield structure 302 includes a plurality of x-ray shielding particles.

In an embodiment, a portion of the intra-oral radiation shield structure 302 extends outwardly beyond a terminal border of an x-ray image detector forming part of the intra-oral x-ray sensor 102. In an embodiment, the intra-oral radiation shield is structured and dimensioned to conform to a portion of an oral cavity. In an embodiment, a portion of the intra-oral radiation shield structure 302 is flexible or jointed so as to conform to a portion of an oral cavity.

Referencing FIG. 3A, in an embodiment, the intra-oral x-ray sensor 102 includes an embedded orientation detection component 316 configured to generate information associated with at least one of an intra-oral x-ray sensor orientation, an intra-oral x-ray sensor position, an intra-oral x-ray sensor dimension, or an intra-oral x-ray sensor centroid position.

In an embodiment, the embedded orientation detection component 316 is operably coupled to one or more orientation sensors 318. For example, in an embodiment, the embedded orientation detection component 316 is operably coupled to one or more magnetic compass based sensors. In an embodiment, the embedded orientation detection component 316 is operably coupled to one or more embedded magnetic compass sensors.

In an embodiment, the embedded orientation detection component 316 is operably coupled to one or more local positioning system based sensors 320. In an embodiment, the embedded orientation detection component 316 is operably coupled to at least two acceleration sensors 322 in a substantially perpendicularly arrangement. In an embodiment, the embedded orientation detection component 316 is operably coupled to at least one gyroscope 324. In an embodiment, the embedded orientation detection component 316 is operably coupled to at least one electrolytic fluid based sensor 326. In an embodiment, the embedded orientation detection component 316 is operably coupled to at least one transmitter (wired or wireless) configured to report position or orientation information to the remote x-ray source 105.

In an embodiment, the embedded orientation detection component 316 is operably coupled to a two-axis tilt sensor 328 configured to detect an intra-oral x-ray sensor pitch angle and an intra-oral x-ray sensor roll angle. In an embodiment, the embedded orientation detection component 316 is operably coupled to at least one multi-axis accelerometer 330. In an embodiment, the embedded orientation detection component 316 is operably coupled to one or more orientation-aware sensors 332.

In an embodiment, the embedded orientation detection component 316 is operably coupled to one or more inductors 334. In an embodiment, the embedded orientation detection component 316 is operably coupled to one or more acoustic transducers 336. In an embodiment, the x-ray image component 116 is operably coupled to one or more dental digital x-ray sensors. In an embodiment, the x-ray image component 116 is operably coupled to one or more dental digital x-ray sensors.

In an embodiment, the x-ray image component 116 is operably coupled to one or more charge-coupled devices 338. In an embodiment, the x-ray image component 116 is operably coupled to one or more active pixel image sensors 340. In an embodiment, the x-ray image component 116 is operably coupled to one or more complementary metal-oxide-semiconductor sensors 342. In an embodiment, the x-ray image component 116 is operably coupled to one or more complementary metal-oxide-semiconductor active pixel sensors 344.

In an embodiment, the intra-oral x-ray sensor 102 includes one or more passive optics devices 204 configured to indicate an intra-oral x-ray sensor border position. In an embodiment, the intra-oral x-ray sensor 102 includes one or more active optic devices 228 (e.g., beacons, acoustic emitters, optical emitters, etc.) configured to generate an output indicative of an intra-oral x-ray sensor border position.

In an embodiment, the intra-oral x-ray sensor 102 includes a beacon component 346 configured to convey information associated with at least one of a sensor position or a sensor orientation. In an embodiment, the beacon component 346 is operably coupled to a transducer configured to generate an output indicative of an intra-oral x-ray sensor border position. In an embodiment, the beacon component 346 is operably coupled to one or more transducers configured to generate an output indicative of an intra-oral x-ray sensor border position. In an embodiment, the beacon component 346 is operably coupled to one or more active optic devices configured to generate an output indicative of an intra-oral x-ray sensor border position. In an embodiment, the beacon component 346 is operably coupled to one or more inductors configured to generate an output indicative of an intra-oral x-ray sensor border position. In an embodiment, the beacon component 346 is operably coupled to one or more accelerometers configured to generate an output indicative of an intra-oral x-ray sensor orientation. In an embodiment, the beacon component 346 is operably coupled to one or more gyroscopes configured to generate an output indicative of an intra-oral x-ray sensor orientation. In an embodiment, the beacon component 346 is operably coupled to one or more electrolytic fluid based sensors 326 configured to generate an output indicative of an intra-oral x-ray sensor orientation.

In an embodiment, the intra-oral x-ray sensor 102 includes an x-ray backscatter component 348 operably coupled to the x-ray image component 116. In an embodiment, the x-ray backscatter component 348 is configured to modify the intra-oral x-ray image information responsive to one or more inputs from the x-ray image component 116 indicative of backscatter, i.e., to computationally remove image noise resulting from backscattered x-rays.

In an embodiment, the intra-oral x-ray sensor 102 includes circuitry 352 configured to communicate intra-oral x-ray sensor position information to a remote x-ray source 105. In an embodiment, communication with the remote x-ray source 105 can be wired or wirelessly connected to the intra-oral x-ray sensor 102. In an embodiment, the circuitry 352 configured to communicate the intra-oral sensor 102 position to the remote x-ray source 105 comprises one or more of a receiver, transmitter, or transceiver. In an embodiment, the circuitry 352 configured to communicate the intra-oral sensor 102 position to the remote x-ray source 105 comprises a wireless transmitter. In an embodiment, the circuitry 352 configured to communicate the intra-oral sensor 102 position is operably coupled to one or more radiation reflecting elements (e.g., prisms retro-reflectors, etc.). In an embodiment, the circuitry 352 configured to communicate the intra-oral sensor 102 position is operably coupled to a modulatable reflector.

In an embodiment, the intra-oral x-ray sensor 102 includes circuitry 354 configured to verify an x-ray beam characteristic associated with the remote x-ray source 105. In an embodiment, the circuitry 354 configured to verify the x-ray beam characteristic associated with the remote x-ray source 105 includes circuitry configured to determine x-ray beam centroid information associated with the remote x-ray source 105. In an embodiment, the circuitry 354 configured to verify the x-ray beam characteristic associated with the remote x-ray source 105 includes circuitry configured to determine a spatial pattern associated with an x-ray beam received from the remote x-ray source 105. In an embodiment, the circuitry 354 configured to verify the x-ray beam characteristic associated with the remote x-ray source 105 includes circuitry configured to determine a spatial alignment associated with an x-ray beam received from the remote x-ray source 105. In an embodiment, the circuitry 354 configured to verify the x-ray beam characteristic associated with the remote x-ray source 105 includes circuitry configured to determine lateral overlap information associated with an x-ray beam received from the remote x-ray source 105 and an intra-oral x-ray sensor 102.

In an embodiment, the intra-oral x-ray sensor 102 includes circuitry 356 configured to communicate an x-ray beam field of view parameter to the remote x-ray source 105 responsive to verifying an x-ray beam characteristic. In an embodiment, the circuitry 356 configured to communicate the x-ray beam field of view parameter to the remote x-ray source 105 comprises one or more of a receiver, transmitter, or transceiver. In an embodiment, the circuitry 356 configured to communicate the x-ray beam field of view parameter to the remote x-ray source 105 comprises a wireless transmitter.

In an embodiment, the intra-oral x-ray sensor 102 includes circuitry 358 configured to generate intra-oral x-ray sensor orientation information. In an embodiment, the circuitry 358 configured to generate intra-oral x-ray sensor orientation information is operably coupled to one or more embedded magnetic compasses. In an embodiment, the circuitry 358 configured to generate the intra-oral x-ray sensor orientation information is operably coupled to one or more electrolytic fluid based sensors 222. In an embodiment, the circuitry 358 configured to generate the intra-oral x-ray sensor orientation information is operably coupled to one or more acceleration sensors. In an embodiment, the circuitry 358 configured to generate the intra-oral x-ray sensor orientation information is operably coupled to one or more multi-axis accelerometers 330. In an embodiment, the circuitry 358 configured to generate the intra-oral x-ray sensor orientation information is operably coupled to at least two acceleration sensors in a substantially perpendicularly arrangement. In an embodiment, the circuitry 358 configured to generate the intra-oral x-ray sensor orientation information is operably coupled to one or more orientation-aware sensors 332.

In an embodiment, the intra-oral x-ray sensor 102 includes circuitry 360 configured to generate intra-oral x-ray sensor position information. In an embodiment, the circuitry 360 configured to generate the intra-oral x-ray sensor position information is operably coupled to one or more local positioning system based sensors. In an embodiment, the circuitry 360 configured to generate the intra-oral x-ray sensor position information is operably coupled to one or more inductors 334. In an embodiment, the circuitry 360 configured to generate the intra-oral x-ray sensor position information is operably coupled to one or more active optic devices (e.g., photodetectors, imagers, CCD detectors, CMOS detectors, etc.). In an embodiment, the circuitry 360 configured to generate the intra-oral x-ray sensor position information is operably coupled to one or more acoustic transducers 336 configured to generate an output indicative of an intra-oral x-ray sensor border position and an intra-oral x-ray sensor orientation. In an embodiment, the circuitry 360 configured to generate the intra-oral x-ray sensor position information is operably coupled to one or more border indicating beacon devices 118.

In an embodiment, the intra-oral x-ray sensor 102 includes circuitry 362 configured to determine remote x-ray source 105 and intra-oral x-ray sensor alignment before communicating an activation instruction to the remote x-ray source 105 for imaging. In an embodiment, the intra-oral x-ray sensor 102 includes circuitry 364 configured to acquire a low intensity x-ray pulse to determine remote x-ray source 105 and intra-oral x-ray sensor alignment before communicating an activation instruction to the remote x-ray source 105 for imaging.

In an embodiment, the intra-oral x-ray sensor 102 includes an integrated component including one or more of the circuitry 352 configured to communicate the intra-oral sensor 102 position is operably coupled to a modulatable reflector; the circuitry 354 configured to verify an x-ray beam characteristic associated with the remote x-ray source 105; the circuitry 356 configured to communicate an x-ray beam field of view parameter to the remote x-ray source 105 responsive to verifying an x-ray beam characteristic; the circuitry 358 configured to generate intra-oral x-ray sensor orientation information; the circuitry 360 configured to generate intra-oral x-ray sensor position information; the circuitry 362 configured to determine remote x-ray source 105; the circuitry 364 configured to acquire a low intensity x-ray pulse to determine remote x-ray source 105 and intra-oral x-ray sensor alignment before communicating an activation instruction to the remote x-ray source 105 for imaging; or the like.

Figure 4A:
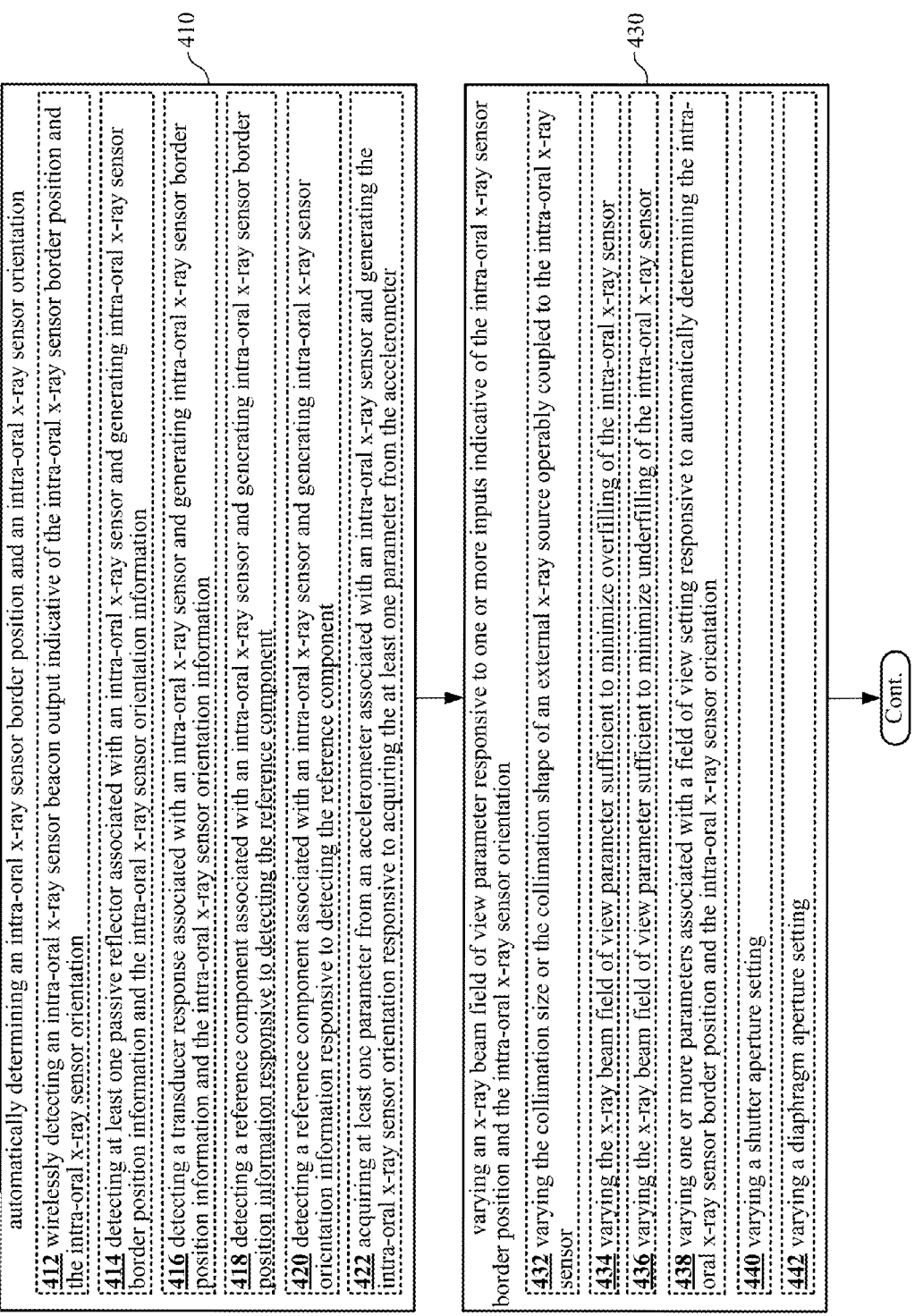
Figure 4C:
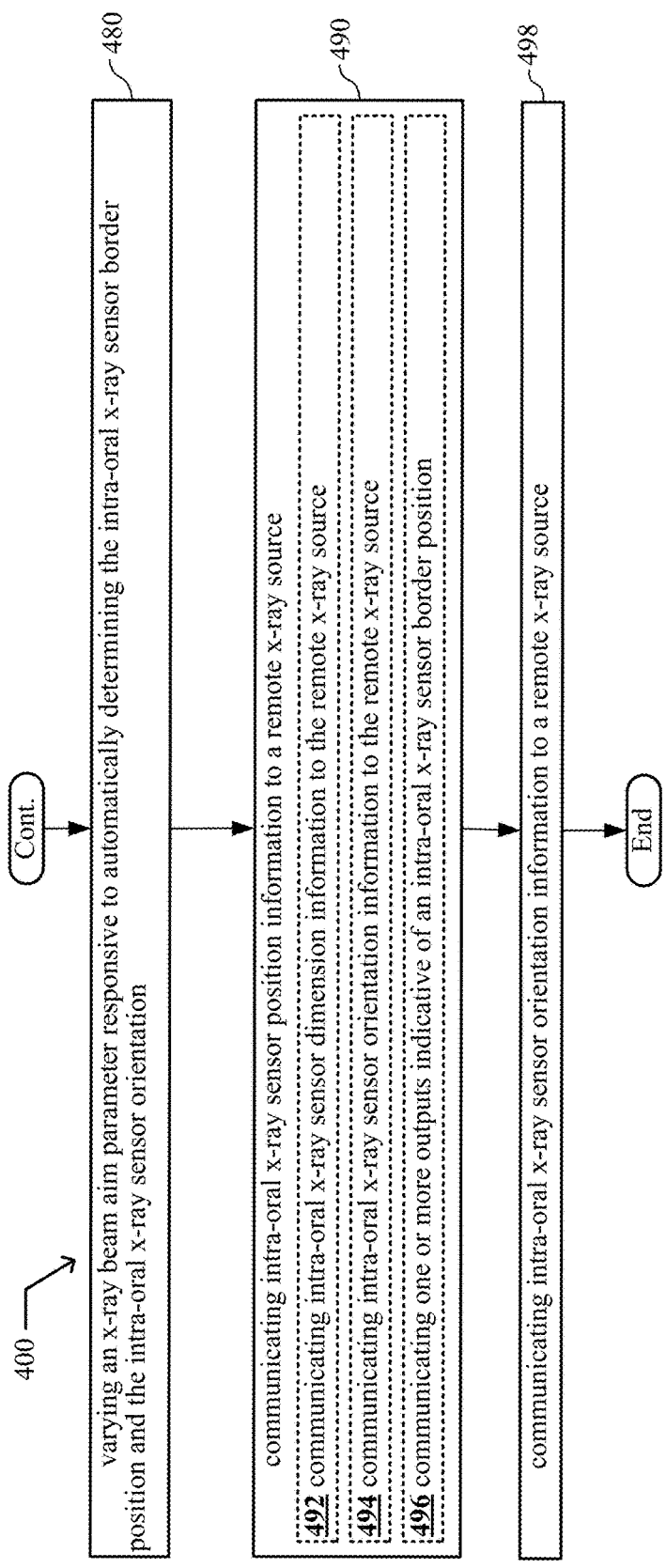

FIGS. 4A-4C show an intra-oral x-ray imaging method 400. At 410, the intra-oral x-ray imaging method 400 includes automatically determining an intra-oral x-ray sensor border position and an intra-oral x-ray sensor orientation. At 412, automatically determining the intra-oral x-ray sensor border position and the intra-oral x-ray sensor orientation includes wirelessly detecting an intra-oral x-ray sensor beacon output indicative of the intra-oral x-ray sensor border position and the intra-oral x-ray sensor orientation. At 414, automatically determining the intra-oral x-ray sensor border position and the intra-oral x-ray sensor orientation includes detecting at least one passive reflector associated with an intra-oral x-ray sensor and generating intra-oral x-ray sensor border position information and intra-oral x-ray sensor orientation information. At 416, automatically determining the intra-oral x-ray sensor border position and the intra-oral x-ray sensor orientation includes detecting a transducer response associated with an intra-oral x-ray sensor 102 and generating intra-oral x-ray sensor border position information and intra-oral x-ray sensor orientation information. At 418, automatically determining the intra-oral x-ray sensor border position and the intra-oral x-ray sensor orientation includes detecting a reference component associated with an intra-oral x-ray sensor 102 and generating intra-oral x-ray sensor border position information responsive to detecting the reference component. At 420, automatically determining the intra-oral x-ray sensor border position and the intra-oral x-ray sensor orientation includes detecting a reference component associated with an intra-oral x-ray sensor 102 and generating intra-oral x-ray sensor orientation information responsive to detecting the reference component. At 422, automatically determining the intra-oral x-ray sensor border position and the intra-oral x-ray sensor orientation includes acquiring at least one parameter from an accelerometer associated with an intra-oral x-ray sensor 102 and generating the intra-oral x-ray sensor orientation responsive to acquiring the at least one parameter from the accelerometer.

At 430, the intra-oral x-ray imaging method 400 includes varying an x-ray beam field of view parameter responsive to one or more inputs including information associated with a location of the intra-oral x-ray sensor border position and the intra-oral x-ray sensor orientation. At 432, varying the x-ray beam field of view parameter responsive to one or more inputs including information associated with an intra-oral x-ray sensor border position and an intra-oral x-ray sensor orientation includes varying the collimation size or the collimation shape of an external x-ray source 105 operably coupled to the intra-oral x-ray sensor 102. At 434, varying the x-ray beam field of view parameter responsive to one or more inputs including information associated with the intra-oral x-ray sensor border position and the intra-oral x-ray sensor orientation includes varying the x-ray beam field of view parameter sufficient to minimize overfilling of the intra-oral x-ray sensor 102. At 436, varying the x-ray beam field of view parameter responsive to one or more inputs including information associated with the intra-oral x-ray sensor border position and the intra-oral x-ray sensor orientation includes varying the x-ray beam field of view parameter sufficient to minimize underfilling of the intra-oral x-ray sensor 102.

At 438, varying the x-ray beam field of view parameter responsive to one or more inputs including information associated with the intra-oral x-ray sensor border position and the intra-oral x-ray sensor orientation includes varying one or more parameters associated with a field of view setting responsive to automatically determining the intra-oral x-ray sensor border position and the intra-oral x-ray sensor orientation. At 440, varying the x-ray beam field of view parameter responsive to one or more inputs including information associated with the intra-oral x-ray sensor border position and the intra-oral x-ray sensor orientation includes varying a shutter aperture setting. At 442, varying the x-ray beam field of view parameter responsive to one or more inputs including information associated with the intra-oral x-ray sensor border position and the intra-oral x-ray sensor orientation includes varying a diaphragm aperture setting.

At 444, varying the x-ray beam field of view parameter responsive to one or more inputs including information associated with the intra-oral x-ray sensor border position and the intra-oral x-ray sensor orientation includes varying a separation between a collimator aperture and an x-ray beam emitter within x-ray source 105. At 446, varying the x-ray beam field of view parameter responsive to one or more inputs including information associated with the intra-oral x-ray sensor border position and the intra-oral x-ray sensor orientation includes varying an orientation between a collimator aperture and an x-ray beam emitter within x-ray source 105. At 448, varying the x-ray beam field of view parameter responsive to one or more inputs including information associated with the intra-oral x-ray sensor border position and the intra-oral x-ray sensor orientation includes actuating one or more selectively actuatable absorber blades forming part of a focal plane shutter.

At 450, varying the x-ray beam field of view parameter responsive to one or more inputs including information associated with the intra-oral x-ray sensor border position and the intra-oral x-ray sensor orientation includes actuating an x-ray beam limiter assembly 108 configured to adjust an x-ray beam field size. At 452, varying the x-ray beam field of view parameter responsive to one or more inputs including information associated with the intra-oral x-ray sensor border position and the intra-oral x-ray sensor orientation includes generating one or more parameters associated with an x-ray beam field size adjustment responsive to automatically determining the intra-oral x-ray sensor border position and the intra-oral x-ray sensor orientation. At 454, varying the x-ray beam field of view parameter responsive to one or more inputs including information associated with the intra-oral x-ray sensor border position and the intra-oral x-ray sensor orientation includes generating one or more x-ray beam limiter assembly 108 setting parameters responsive to automatically determining the intra-oral x-ray sensor border position and the intra-oral x-ray sensor orientation. At 456, varying the x-ray beam field of view parameter responsive to one or more inputs including information associated with the intra-oral x-ray sensor border position and the intra-oral x-ray sensor orientation includes actuating at least one liquid absorber.

At 460, the intra-oral x-ray imaging method 400 includes acquiring intra-oral x-ray image information associated with a patient. At 462, acquiring the intra-oral x-ray image information associated with the patient includes acquiring one or more intra-oral radiographic images. At 464, acquiring the intra-oral x-ray image information associated with the patient includes acquiring intra-oral radiographic view information. At 466, acquiring the intra-oral x-ray image information associated with the patient includes acquiring a periapical view image of at least one anterior or posterior tooth. At 468, acquiring the intra-oral x-ray image information associated with the patient includes acquiring a bitewing view image of at least one tooth crown. At 470, acquiring the intra-oral x-ray image information associated with the patient includes acquiring an occlusal view image of a palate. At 472, acquiring the intra-oral x-ray image information associated with the patient includes acquiring a posterior periapical image. At 474, acquiring the intra-oral x-ray image information associated with the patient includes acquiring an anterior periapical image.

At 478, the intra-oral x-ray imaging method 400 includes generating at least one parameter associated with an x-ray imaging mode (e.g., adult panoramic mode, child panoramic mode, high-dose-rate mode, low-dose-rate mode, moderate-dose-rate mode mandible mode, occlusion mode, maxillary mode, panoramic mode, pulsed fluoroscopy mode, temporo-mandibular joint mode, etc.) responsive to automatically determining the intra-oral x-ray sensor border position and the intra-oral x-ray sensor orientation.

At 480, the intra-oral x-ray imaging method 400 includes varying an x-ray beam aim parameter responsive to automatically determining the intra-oral x-ray sensor border position and the intra-oral x-ray sensor orientation. At 490, the intra-oral x-ray imaging method 400 includes communicating intra-oral x-ray sensor position information to a remote x-ray source 105. At 492, communicating the intra-oral x-ray sensor position information to the remote x-ray source 105 includes communicating intra-oral x-ray sensor dimension information to the remote x-ray source 105. At 494, communicating the intra-oral x-ray sensor position information to the remote x-ray source 105 includes communicating intra-oral x-ray sensor orientation information to the remote x-ray source 105. At 496, communicating the intra-oral x-ray sensor position information to the remote x-ray source 105 includes communicating one or more outputs indicative of an intra-oral x-ray sensor border position. At 498, the intra-oral x-ray imaging method 400 includes communicating intra-oral x-ray sensor orientation information to a remote x-ray source 105.

FIG. 5 shows an intra-oral x-ray sensor operation method 500. At 510, the intra-oral x-ray sensor operation method 500 includes verifying an x-ray beam characteristic associated with the remote x-ray source 105. At 520, the intra-oral x-ray sensor operation method 500 includes communicating an x-ray beam field of view parameter to the remote x-ray source 105 responsive to verifying an x-ray beam characteristic. At 522, communicating the x-ray beam field of view parameter to the remote x-ray source 105 includes communicating a parameter associated with a change in separation between a collimator aperture 114 and the remote x-ray source 105. At 524, communicating the x-ray beam field of view parameter to the remote x-ray source 105 includes communicating a parameter associated with actuating one or more electro-mechanical collimation edges. At 526, communicating the x-ray beam field of view parameter to the remote x-ray source 105 includes communicating a parameter associated with displacing, moving, or rotating one or more collimation edges. At 528 communicating the x-ray beam field of view parameter to the remote x-ray source 105 includes communicating a parameter associated with adjusting a relative position of an x-ray beam emitter within the remote x-ray source 105 and a collimator 110 to improve alignment of the x-ray beam to the sensor.

At 530, the intra-oral x-ray sensor operation method 500 includes activating a discovery protocol that allows an intra-oral x-ray sensor 102 and the remote x-ray source 105 to identify each other and to negotiate information. At 540, the intra-oral x-ray sensor operation method 500 includes determining a remote x-ray source 105 and intra-oral x-ray sensor alignment. At 550, the intra-oral x-ray sensor operation method 500 includes communicating an activation instruction to the remote x-ray source 105 for imaging responsive to determining the remote x-ray source 105 and intra-oral x-ray sensor 102 alignment. At 560, the intra-oral x-ray sensor operation method 500 includes detecting a low intensity x-ray pulse to determine remote x-ray source 105 and intra-oral x-ray sensor alignment. At 570, the intra-oral x-ray sensor operation method 500 includes communicating an activation instruction to the remote x-ray source 105 for imaging responsive to detecting the low intensity x-ray pre-pulse to determine remote the x-ray source 105 and intra-oral x-ray sensor 102 alignment.

It is noted that FIGS. 4A-4C and 5 denotes "start" and "end" positions. However, nothing herein should be construed to indicate that these are limiting and it is contemplated that other or additional steps or functions can occur before or after those described in FIGS. 4A-4C and 5.

The claims, description, and drawings of this application may describe one or more of the instant technologies in operational/functional language, for example as a set of operations to be performed by a computer. Such operational/functional description in most instances can be specifically-configured hardware (e.g., because a general purpose computer in effect becomes a special purpose computer once it is programmed to perform particular functions pursuant to instructions from program software).

Importantly, although the operational/functional descriptions described herein are understandable by the human mind, they are not abstract ideas of the operations/functions divorced from computational implementation of those operations/functions. Rather, the operations/functions represent a specification for the massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to the human mind. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail in the following paragraphs, these logical operations/functions are not representations of abstract ideas, but rather representative of static or sequenced specifications of various hardware elements. Differently stated, unless context dictates otherwise, the logical operations/functions are representative of static or sequenced specifications of various hardware elements. This is true because tools available to implement technical disclosures set forth in operational/functional formats—tools in the form of a high-level programming language (e.g., C, java, visual basic), etc.), or tools in the form of Very high speed Hardware Description Language ("VIDAL," which is a language that uses text to describe logic circuits—)—are generators of static or sequenced specifications of various hardware configurations. This fact is sometimes obscured by the broad term "software," but, as shown by the following explanation, what is termed "software" is a shorthand for a massively complex interchanging/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. See, e.g., *High-level Programming Language., Wikipedia*. Wikimedia Foundation, 18 Jan. 2014. Web. 4 Feb. 2014. In order to facilitate human comprehension, in many instances, high-level programming languages resemble or even share symbols with natural languages. See, e.g., *Natural Language., Wikipedia*. Wikimedia Foundation, 14 Jan. 2014. Web. 4 Feb. 2014.

It has been argued that because high-level programming languages use strong abstraction (e.g., that they may resemble or share symbols with natural languages), they are therefore a "purely mental construct" (e.g., that "software"—a computer program or computer—programming—is somehow an ineffable mental construct, because at a high level of abstraction, it can be conceived and understood in the human mind). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In an embodiment, if a high-level programming language is the tool used to implement a technical disclosure in the form of functions/operations, it can be understood that, far from being abstract, imprecise, "fuzzy," or "mental" in any significant semantic sense, such a tool is instead a near incomprehensibly precise sequential specification of specific computational—machines—the parts of which are built up by activating/selecting such parts from typically more general computational machines over time (e.g., clocked time). This fact is sometimes obscured by the superficial similarities between high-level programming languages and natural languages. These superficial similarities also may cause a glossing over of the fact that high-level programming language implementations ultimately perform valuable work by creating/controlling many different computational machines.

The many different computational machines that a high-level programming language specifies are almost unimaginably complex. At base, the hardware used in the computational machines typically consists of some type of ordered matter (e.g., traditional electronic devices (e.g., transistors), deoxyribonucleic acid (DNA), quantum devices, mechanical switches, optics, fluidics, pneumatics, optical devices (e.g., optical interference devices), molecules, etc.) that are arranged to form logic gates. Logic gates are typically physical devices that may be electrically, mechanically, chemically, or otherwise driven to change physical state in order to create a physical reality of Boolean logic.

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory devices, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors). See, e.g., *Logic Gates., Wikipedia*. Wikimedia Foundation, 2 Apr. 2014. Web. 4 Feb. 2014.

The logic circuits forming the microprocessor are arranged to provide a microarchitecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output. See, e.g., *Computer Architecture., Wikipedia*. Wikimedia Foundation, 2 Feb. 2014. Web. 4 Feb. 2014.

The Instruction Set Architecture includes a specification of the machine language that can be used by programmers to use/control the microprocessor. Since the machine language instructions are such that they may be executed directly by the microprocessor, typically they consist of strings of binary digits, or bits. For example, a typical machine language instruction might be many bits long (e.g., 32, 64, or 128 bit strings are currently common). A typical machine language instruction might take the form "11110000101011110000111100111111" (a 32 bit instruction).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configuration, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

Machine language is typically incomprehensible by most humans (e.g., the above example was just ONE instruction, and some personal computers execute more than two billion instructions every second). See, e.g., *Instructions per Second., Wikipedia*. Wikimedia Foundation, 13 Jan. 2014. Web. 4 Feb. 2014.

Thus, programs written in machine language—which may be tens of millions of machine language instructions long—are incomprehensible. In view of this, early assembly languages were developed that used mnemonic codes to refer to machine language instructions, rather than using the machine language instructions' numeric values directly (e.g., for performing a multiplication operation, programmers coded the abbreviation "mult," which represents the binary number "011000" in MIPS machine code). While assembly languages were initially a great aid to humans controlling the microprocessors to perform work, in time the complexity of the work that needed to be done by the humans outstripped the ability of humans to control the microprocessors using merely assembly languages.

At this point, it was noted that the same tasks needed to be done over and over, and the machine language necessary to do those repetitive tasks was the same. In view of this, compilers were created. A compiler is a device that takes a statement that is more comprehensible to a human than either machine or assembly language, such as "add 2+2 and output the result," and translates that human understandable statement into a complicated, tedious, and immense machine language code (e.g., millions of 32, 64, or 128 bit length strings). Compilers thus translate high-level programming language into machine language.

This compiled machine language, as described above, is then used as the technical specification which sequentially constructs and causes the interoperation of many different computational machines such that humanly useful, tangible, and concrete work is done. For example, as indicated above, such machine language—the compiled version of the higher-level language—functions as a technical specification which selects out hardware logic gates, specifies voltage levels, voltage transition timings, etc., such that the humanly useful work is accomplished by the hardware.

Thus, a functional/operational technical description, when viewed by one of skill in the art, is far from an abstract idea. Rather, such a functional/operational technical description, when understood through the tools available in the art such as those just described, is instead understood to be a humanly understandable representation of a hardware specification, the complexity and specificity of which far exceeds the comprehension of most any one human. Accordingly, any such operational/functional technical descriptions may be understood as operations made into physical reality by (a) one or more interchained physical machines, (b) interchained logic gates configured to create one or more physical machine(s) representative of sequential/combinatorial logic(s), (c) interchained ordered matter making up logic gates (e.g., interchained electronic devices (e.g., transistors), DNA, quantum devices, mechanical switches, optics, fluidics, pneumatics, molecules, etc.) that create physical reality representative of logic(s), or (d) virtually any combination of the foregoing. Indeed, any physical object which has a stable, measurable, and changeable state may be used to construct a machine based on the above technical description. Charles Babbage, for example, constructed the first computer out of wood and powered by cranking a handle.

Thus, far from being understood as an abstract idea, it can be recognizes that a functional/operational technical description as a humanly-understandable representation of one or more almost unimaginably complex and time sequenced hardware instantiations. The fact that functional/operational technical descriptions might lend themselves readily to high-level computing languages (or high-level block diagrams for that matter) that share some words, structures, phrases, etc. with natural language simply cannot be taken as an indication that such functional/operational technical descriptions are abstract ideas, or mere expressions of abstract ideas. In fact, as outlined herein, in the technological arts this is simply not true. When viewed through the tools available to those of skill in the art, such functional/operational technical descriptions are seen as specifying hardware configurations of almost unimaginable complexity.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

The use of functional/operational technical descriptions assists the person of skill in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person of skill in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those of skill in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such, and should not be disparagingly characterized as abstract ideas merely because the specifications they represent are presented in a manner that one of skill in the art can readily understand and apply in a manner independent of a specific vendor's hardware implementation.

At least a portion of the devices or processes described herein can be integrated into an information processing system. An information processing system generally includes one or more of a system unit housing, a video display device, memory, such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), or control systems including feedback loops and control motors (e.g., feedback for detecting position or velocity, control motors for moving or adjusting components or quantities). An information processing system can be implemented utilizing suitable commercially available components, such as those typically found in data computing/communication or network computing/communication systems.

The state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Various vehicles by which processes or systems or other technologies described herein can be effected (e.g., hardware, software, firmware, etc., in one or more machines or articles of manufacture), and that the preferred vehicle will vary with the context in which the processes, systems, other technologies, etc., are deployed. For example, if an implementer determines that speed and accuracy are paramount, the implementer may opt for a mainly hardware or firmware vehicle; alternatively, if flexibility is paramount, the implementer may opt for a mainly software implementation that is implemented in one or more machines or articles of manufacture; or, yet again alternatively, the implementer may opt for some combination of hardware, software, firmware, etc. in one or more machines or articles of manufacture. Hence, there are several possible vehicles by which the processes, devices, other technologies, etc., described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. In an embodiment, optical aspects of implementations will typically employ optically-oriented hardware, software, firmware, etc., in one or more machines or articles of manufacture.

The herein described subject matter sometimes illustrates different components contained within, or connected with, different other components. It is to be understood that such depicted architectures are merely examples, and that in fact, many other architectures can be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include, but are not limited to, physically mateable, physically interacting components, wirelessly interactable, wirelessly interacting components, logically interacting, logically interactable components, etc.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components, or inactive-state components, or standby-state components, unless context requires otherwise.

The foregoing detailed description has set forth various embodiments of the devices or processes via the use of block diagrams, flowcharts, or examples. Insofar as such block diagrams, flowcharts, or examples contain one or more functions or operations, it will be understood by the reader that each function or operation within such block diagrams, flowcharts, or examples can be implemented, individually or collectively, by a wide range of hardware, software, firmware in one or more machines or articles of manufacture, or virtually any combination thereof. Further, the use of "Start," "End," or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein is implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Non-limiting examples of a signal-bearing medium include the following: a recordable type medium such as a floppy disk, a hard disk drive, a Compact Disc (CD), a Digital Video Disk (DVD), a digital tape, a computer memory, etc.; and a transmission type medium such as a digital or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to the reader that, based upon the teachings herein, changes and modifications can be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings includes overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. An intra-oral x-ray imaging system, comprising:
an intra-oral x-ray sensor configured to acquire intra-oral x-ray image information associated with an oral cavity of a patient, the intra-oral x-ray sensor including an intra-oral radiation shield structure having at least a portion that is flexible or jointed so as to conform to a portion of the oral cavity; and
an x-ray beam limiter assembly including a controllable x-ray collimator module, the controllable x-ray collimator module including an x-ray beam collimation adjustment mechanism responsive to one or more inputs including information associated with a border location of the intra-oral x-ray sensor in a mouth of the patient.

2. The intra-oral x-ray imaging system of claim 1, wherein the x-ray collimator module is operably coupled to the intra-oral x-ray sensor, and is configured to adjust an x-ray beam field of view responsive to one or more inputs from the intra-oral x-ray sensor indicative of a border position of the intra-oral x-ray sensor.

3. The intra-oral x-ray imaging system of claim 1, wherein the x-ray collimator module is operably coupled to one or more sensors configured to determine a border position of the intra-oral x-ray sensor.

4. The intra-oral x-ray imaging system of claim 1, wherein the x-ray beam limiter assembly further comprises one or more shutters; and wherein the x-ray collimator module is configured to vary a shutter aperture associated with at least one of the one or more shutters responsive to the one or more inputs.

5. The intra-oral x-ray imaging system of claim 1, wherein the x-ray beam limiter assembly further comprises a plurality of selectively actuatable absorber blades configured to form a shutter; and wherein the x-ray collimator module is configured to adjust the x-ray beam field size by actuating one or more of the plurality of selectively actuatable absorber blades responsive to the one or more inputs.

6. The intra-oral x-ray imaging system of claim 1, wherein the x-ray beam limiter assembly further comprises a variable aperture collimator.

7. The intra-oral x-ray imaging system of claim 1, wherein the x-ray beam limiter assembly further comprises at least a first-stage shutter and a second-stage shutter.

8. The intra-oral x-ray imaging system of claim 1, wherein the x-ray beam limiter assembly further comprises one or more shutters formed from high atomic number (high-Z) materials.

9. The intra-oral x-ray imaging system of claim 1, wherein the x-ray beam limiter assembly further comprises one or more positive beam limitation devices.

10. The intra-oral x-ray imaging system of claim 1, wherein at least one of the one or more inputs is indicative of a corner position of the intra-oral x-ray sensor.

11. The intra-oral x-ray imaging system of claim 1, wherein at least one of the one or more inputs is indicative of an edge position of the intra-oral x-ray sensor.

12. The intra-oral x-ray imaging system of claim 1, wherein at least one of the one or more inputs is indicative of a reference position on the intra-oral x-ray sensor having a specified offset from an edge of the intra-oral x-ray sensor.

13. The intra-oral x-ray imaging system of claim 1, wherein at least one of the one or more inputs is indicative of an edge orientation of the intra-oral x-ray sensor.

14. The intra-oral x-ray imaging system of claim 1, wherein the x-ray collimator module is configured to adjust the x-ray beam field of view responsive to one or more inputs from a field of view module indicative of an intra-oral x-ray sensor position and orientation.

15. The intra-oral x-ray imaging system of claim 1, wherein the x-ray collimator module is configured to generate at least one parameter associated with an x-ray imaging mode responsive to one or more inputs from the intra-oral x-ray sensor.

16. The intra-oral x-ray imaging system of claim 1, further comprising:
a field of view module operable to generate one or more parameters associated with a field of view setting responsive to one or more inputs from the x-ray collimator module indicative of an intra-oral x-ray sensor position and orientation.

17. The intra-oral x-ray imaging system of claim 1, further comprising:
an intra-oral x-ray sensor module operably coupled to the x-ray image sensor and the x-ray collimator module, the intra-oral x-ray sensor module configured to generate one or more of intra-oral x-ray sensor dimension information, intra-oral x-ray sensor orientation information, or intra-oral x-ray sensor position information responsive to one or more inputs from the x-ray image sensor or the x-ray collimator module.

18. The intra-oral x-ray imaging system of claim 1, further comprising a camera configured to acquire at least one of the inputs.

19. The intra-oral x-ray imaging system of claim 18, wherein the intra-oral x-ray sensor comprises at least one beacon; and
wherein the camera is configured to acquire an input associated with a position of the least one beacon.

20. The intra-oral x-ray imaging system of claim 1, wherein the intra-oral x-ray sensor comprises a position sensor configured to determine border position data, and a transmitter configured to transmit a signal indicative of the border position data.

21. The intra-oral x-ray imaging system of claim 1, wherein the x-ray collimator module is configured to adjust the x-ray beam field to maximize an amount of the x-ray beam which impacts the intra-oral x-ray sensor.

22. An intra-oral x-ray imaging device, comprising:
circuitry configured to determine a position and an orientation of an intra-oral x-ray sensor;
circuitry configured to receive an x-ray beam characteristic verified by the intra-oral x-ray sensor, the x-ray beam characteristic associated with an x-ray transmitted to the intra-oral x-ray sensor;
circuitry configured to adjust an x-ray beam collimation adjustment mechanism of an x-ray beam limiter assembly responsive to one or more inputs from at least one of the circuitry configured to determine the position and the orientation of the intra-oral x-ray sensor or the circuitry configured to receive an x-ray beam characteristic verified by the intra-oral x-ray sensor; and
circuitry configured to acquire intra-oral x-ray image information associated with a patient.

23. The intra-oral x-ray imaging device of claim 22, wherein the circuitry configured to determine the position and the orientation of the intra-oral x-ray sensor includes circuitry configured to determine border position information of the intra-oral x-ray sensor.

24. The intra-oral x-ray imaging device of claim 22, wherein the circuitry configured to determine the position and the orientation of the intra-oral x-ray sensor includes circuitry configured to determine an intra-oral x-ray sensor centroid position.

25. The intra-oral x-ray imaging device of claim 22, wherein the circuitry configured to determine the position and the orientation of the intra-oral x-ray sensor is operably coupled to an image sensor configured to detect one or more optic devices indicative of an intra-oral x-ray sensor border position, an intra-oral x-ray sensor position, or an intra-oral x-ray sensor orientation.

26. The intra-oral x-ray imaging device of claim 22, wherein the circuitry configured to determine the position and the orientation of the intra-oral x-ray sensor is operably coupled to an embedded orientation detection component.

27. The intra-oral x-ray imaging device of claim 22, wherein the circuitry configured to determine the position and the orientation of the intra-oral x-ray sensor is operably coupled to one or more local positioning system based sensors.

28. The intra-oral x-ray imaging device of claim 22, wherein the circuitry configured to determine the position and the orientation of the intra-oral x-ray sensor is operably coupled to one or more multi-axis accelerometers.

29. The intra-oral x-ray imaging device of claim 22, wherein the circuitry configured to determine the position and the orientation of the intra-oral x-ray sensor is operably coupled to one or more electrolytic fluid based sensors.

30. The intra-oral x-ray imaging device of claim 22, wherein the circuitry configured to determine the position and the orientation of the intra-oral x-ray sensor is operably coupled to one or more acoustic transducers configured to generate an output indicative of an intra-oral x-ray sensor border position and an intra-oral x-ray sensor orientation.

31. The intra-oral x-ray imaging device of claim 22, further comprising:
circuitry configured to generate one or more parameters associated with a field of view setting.

32. An intra-oral x-ray imaging method, comprising:
automatically determining an intra-oral x-ray sensor border position and an intra-oral x-ray sensor orientation of an intra-oral x-ray sensor;
transmitting an x-ray to the intra-oral sensor;
receiving an x-ray beam characteristic verified by the intra-oral x-ray sensor responsive to transmitting the x-ray to the intra-oral x-ray sensor;
varying an x-ray beam collimation parameter via an x-ray beam collimation adjustment mechanism of an x-ray beam limiter assembly responsive to one or more inputs including information associated with at least one of the intra-oral x-ray sensor border position and the intra-oral x-ray sensor orientation or the x-ray beam characteristic verified by the intra-oral x-ray sensor; and
acquiring intra-oral x-ray image information associated with a patient.

33. The intra-oral x-ray imaging method of claim 32, wherein automatically determining the intra-oral x-ray sensor border position and the intra-oral x-ray sensor orientation of the intra-oral x-ray sensor includes wirelessly detecting an intra-oral x-ray sensor beacon output indicative of the intra-oral x-ray sensor border position and the intra-oral x-ray sensor orientation.

34. The intra-oral x-ray imaging method of claim 32, wherein automatically determining the intra-oral x-ray sensor border position and the intra-oral x-ray sensor orientation of the intra-oral x-ray sensor includes detecting a transducer response associated with the intra-oral x-ray sensor and generating intra-oral x-ray sensor border position information and the intra-oral x-ray sensor orientation information.

35. The intra-oral x-ray imaging method of claim 32, wherein varying the x-ray beam collimation parameter via an x-ray beam collimation adjustment mechanism of a controllable x-ray collimator module of an x-ray beam limiter assembly responsive to one or more inputs including information associated with at least one of the intra-oral x-ray sensor border position and the intra-oral x-ray sensor orientation or the x-ray beam characteristic verified by the intra-oral x-ray sensor includes varying a collimation size or a collimation shape of an external x-ray source operably coupled to the intra-oral x-ray sensor.

36. The intra-oral x-ray imaging method of claim 32, further comprising:
generating at least one parameter associated with an x-ray imaging responsive to automatically determining the intra-oral x-ray sensor border position and the intra-oral x-ray sensor orientation.

37. The intra-oral x-ray imaging method of claim 32, further comprising:
varying an x-ray beam aim parameter responsive to automatically determining the intra-oral x-ray sensor border position and the intra-oral x-ray sensor orientation.

38. The intra-oral x-ray imaging system of claim 1, wherein the x-ray beam limiter assembly further comprises one or more x-ray compensating filters.

* * * * *